(12) United States Patent
Solomon et al.

(10) Patent No.: US 7,169,847 B2
(45) Date of Patent: Jan. 30, 2007

(54) POLYMERIC MEMBRANES AND USES THEREOF

(75) Inventors: David Henry Solomon, Officer Victoria (AU); Marcus Julian Caulfield, Ashburton Victoria (AU); Helen Katherine Purss, Vermont South Victoria (AU)

(73) Assignee: Life Therapeutics, Inc., Clarkston, GA (US)

( * ) Notice: Subject to any disclaimer, the term of this patent is extended or adjusted under 35 U.S.C. 154(b) by 5 days.

(21) Appl. No.: 10/085,658

(22) Filed: Feb. 27, 2002

(65) Prior Publication Data
US 2005/0009994 A1    Jan. 13, 2005

(30) Foreign Application Priority Data
Feb. 27, 2001    (AU) .................................... PR 3407

(51) Int. Cl.
*C08F 16/06*    (2006.01)
*C08F 116/06*    (2006.01)

(52) U.S. Cl. ....................... 525/56; 525/61; 525/328.8; 525/328.9

(58) Field of Classification Search ................. 525/56, 525/61, 328.8, 328.9
See application file for complete search history.

(56) References Cited

U.S. PATENT DOCUMENTS 3,844,926 A    10/1974    Smyth et al.
4,149,957 A    4/1979    Gibson et al.
4,798,674 A    1/1989    Pasternak et al.

FOREIGN PATENT DOCUMENTS

| | | |
|---|---|---|
| DE | 19545701 | 5/1997 |
| EP | 0274387 | 7/1988 |
| EP | 0460769 | 12/1991 |
| EP | 0311882 | 6/1992 |
| GB | 2174619 | 11/1986 |
| JP | 2171705 | 7/1987 |
| JP | 3126504 | 5/1988 |
| JP | 2174924 | 7/1990 |
| JP | 7185278 | 7/1995 |
| WO | WO 79/0002 | 1/1979 |
| WO | WO 91/04085 | 4/1991 |
| WO | WO 97/17129 * | 5/1997 |
| WO | WO 00/43115 | 7/2000 |

* cited by examiner

*Primary Examiner*—Robert D. Harlan
(74) *Attorney, Agent, or Firm*—Cooley Godward Kronish LLP

(57) ABSTRACT

A polymeric membrane suitable for use in electrophoresis formed from a pre-polymer having a plurality of crosslinkable moieties and the crosslinkable moieties being crosslinked with a polyfunctional crosslinking agent.

51 Claims, 13 Drawing Sheets

POLYMERIC MEMBRANES AND USES THEREOF

FIELD

The present application generally relates to polymeric membranes. In particular, the present application relates to gel membranes and their use in, but not limited to, electrophoretic techniques and the like, methods of making such membranes and articles made and formed therefrom.

BACKGROUND

The development of new polymeric membranes is an area of intense commercial interest because of their usefulness in many different applications. Membranes can be defined as selective barriers between two phases. Efficient separation is achieved by the differential rate of movement of molecules, and is dependent on the properties of the separation medium, for example, porosity, pore size distribution, thickness, hydrophilicity, membrane fouling, etc. Examples of the driving force for the movement of molecules across membranes includes concentration differences, pressure differences and electric potential difference (e.g., electrophoresis-based systems).

A wide variety of different materials has been utilized for producing membranes. In general, microporous membranes can be divided into two main groups: those formed physically and those formed chemically. Physically formed membranes can be controllably formed by careful manipulation of the solubility of polymers in solution. These physically formed membranes may be produced by diffusion induced phase separation techniques (DIPS) or temperature induced phase separation (TIPS). Physically formed membranes are useful for many applications including water purification, dialysis and protein separation. However, the techniques for reliably producing physically formed membranes of controlled pore size distribution can be complicated, expensive and not easily reproduced in the laboratory.

Chemically produced membranes may be made via a series of chemical reactions to form very thin three-dimensional polymeric networks. Because these thin polymeric networks generally lack mechanical strength, they are often supported by a substrate that provides the membrane with the requisite mechanical strength. Examples of such membranes include those formed from acrylics, vinylics, methyl methacrylates/ethylene glycol dimethacrylate (EGDMA) and acrylamide (AAm)/N,N'-methylene-bis-acrylamide (Bis) networks. Polymer membranes have been formed by free radical chain polymerization. Unfortunately, free radical reactions are difficult to control, resulting in unwanted side reactions and charged groups.

Membranes are utilized in a wide variety of applications, and are particularly useful in electrophoretic techniques. For example, one membrane-based electrophoresis technique (e.g., Gradiflow™ (Gradipore, Australia)) involves a fixed boundary preparative electrophoresis method (U.S. Pat. Nos. 5,650,055, 5,039,386 and WO 0013776). This technique utilizes a semi-permeable membrane to separate two streams of macromolecules—(e.g., proteins, DNA, RNA, etc) containing liquids. When an electric potential is applied across the membrane, charged species tend to move in the direction of one of the electrodes. If the charged species are positively charged, they tend to move towards the negative electrode (cathode), conversely, negatively charged species move towards the positive electrode (anode). Careful selection of the properties of the membrane (e.g., pore size distribution) will facilitate the separation of the desired charged macromolecules. Cooling of the solutions is accomplished by circulation of chilled buffer solutions that are separated by two further membranes, hereafter referred to as restriction membranes, and are situated between the electrodes and the separation membranes. The restriction membranes allow the passage of ions but not macromolecules.

Depending on the choice of separation apparatus, separation media, and buffer characteristics, electrophoretic techniques can be used in one or more of at least four different modes: (1) charged-based separation, (2) size-based separation, (3) concentration, and (4) dialysis. There are electrophoresis separation techniques available that can separate compounds on the basis of only one mode whereas the Gradiflow™ is adaptable for separation in each of all four modes by selecting appropriate separation media and electrophoresis conditions.

Hydrogel membranes are currently used in some existing electrophoretic systems. For example, the Gradiflow™ method utilizes a thin polyacrylamide (PAAm) hydrogel membrane with a defined pore size (D. B. Rylatt, M. Napoli, D. Ogle, A. Gilbert, S. Lim, and C. H. Nair, *J. Chromatog., A*, 865, 145–153, 1999). The membrane is produced via the free radical co-polymerization of a monomer such as acrylamide (AAm) and a polyfunctional crosslinking agent such as N,N'-methylene-bis-acrylamide (Bis). In general, hydrogels are desirable because they are reasonably strong, flexible, chemically inert, bio-compatible and can be made with relatively controlled pore structure for most applications.

Recent work has facilitated advances into producing other polymeric networks as well as improved PAAm gels. One approach has focused on altering the nature of the monomers used, including changing the polyfunctional crosslinking agent, for example in the case of PAAm gels, substitution of Bis for another monomer can lead to a different network structure.(M. G. Harrington and T. E. Zewert, *Electrophoresis*, 15, 195–199, 1994; G. Y. N. Chan, P. A. Kambouris, M. G. Looney, G. G. Qiao, and D. H. Solomon, *Polymer*, 41, 27–34, 2000; G. Patras, G. G. Qiao, and D. Solomon, H., *Electrophoresis*, 21, 3843–3850, 2000). However, due to the free radical nature of the polymerization, the chemistries involved are difficult to control and often result in undesirable defects in the gel. For example, failure to control the reaction conditions of the polymerization can lead to charged groups within the network and reduced stability, thereby decreasing the yield of the reaction and increasing the costs of producing a suitable gel.

Currently, the pore size range of commercially available membranes is somewhat limited. For example, large pores suitable for DNA and RNA separations are not routinely available. Some of the unsolved problems remaining with conventional electrophoresis membranes include producing membranes with no or an insignificant degree of charged groups, the ability to control pore size over a wide range of pore sizes and the development of stable gels over a wide pH range.

Thus, a need exists for polymeric membranes with increased stability, decreased number of charge groups within the gel, that are cost efficient to make, and can be manufactured with increased production yields. It would therefore be beneficial to develop polymeric membranes having one or more properties such as controllable pore sizes, good processability, reproducability, high resistance to degradation, bio-stability and bio-compatibility, and preferably, without one or more disadvantages of existing systems.

SUMMARY

Aspects of the present application greatly alleviate one or more of the disadvantages of known polymeric membranes by providing a polymeric membrane having a number of desirable properties such as controllable pore sizes, good processability, reproducibility, high resistance to degradation, bio-stability or bio-compatibility. Other aspects provide a method of forming a polymeric membrane and a method of separating molecules using embodiments of the polymeric membrane under separating conditions such as electrophoresis. As such, embodiments of polymeric membrane described herein may be used, for example, as an electrophoretic medium, an electrophoretic cartridge, or as an electrophoretic device for separating molecules.

In one embodiment, a polymeric membrane results from the reaction that includes a pre-polymer. The pre-polymer has a number crosslinkable moieties and these crosslinkable moieties are crosslinked to a polyfunctional cross linking agent. In another embodiment, a method of making a polymeric membrane involves providing a pre-polymer and contacting the pre-polymer with a polyfunctional crosslinking agent to form a polymeric membrane.

Unlike conventional free radical polymerization in which the crosslinked membrane is formed entirely by chain growth, some embodiments of the polymeric membrane are a result of the reaction of a pre-polymer that is crosslinked by a step-growth reaction with a polyfunctional crosslinking agent. This step-growth type of approach to forming a polymeric network allows for greater control over the properties of the polymeric network. As such, the polymeric membrane and methods used to form the polymeric membrane avoid the difficulties inherent to free radical chain reactions.

Advantageously, embodiments of the polymeric membrane may be used in electrophoretic separation techniques. One aspect provides an electrophoretic medium for use in an electrophoretic technique. For example, the electrophoretic medium may be a free-standing gel membrane, or supported by a substrate such as a cartridge.

Another aspect of the present application involves the addition of charged coordinating agents. This results in an overall negative charge on the membrane surface, giving rise to a net flux of buffer ions from the cathodic stream (stream 1) to the anodic stream (stream 2), and, in turn, favorably altering the electroendosmotic flow. Advantageously, the buffer-membrane interaction of the polymeric membrane may be used to control electrophoretic transfer or the rate of endosmosis.

In another aspect, the addition of a hydrogen bond breaker provides another advantage over existing membranes and separation devices. The addition of a hydrogen bond breaker may disrupt the existing inter-and intramolecular hydrogen bonding of the hydroxyl groups of the pre-polymer. Advantageously, this results in enhanced interaction between crosslinkable moieties such as hydroxyls and the charged coordinating agent.

Another aspect of the present application provides for a method of separating molecules by providing a polymeric membrane described in the present application, and separating a sample of molecules using a separation technique. For example, this separation method may be used to separate charged species and biomolecules such as proteins, peptides, DNA, or RNA. As a non-limiting example, the separation technique may be electrophoresis. Embodiments of the application also include other electrophoretic devices.

These and other aspects will be appreciated from review of the following embodiments and aspects described below, along with the accompanying figures in which like reference numerals refer to like parts throughout.

DETAILED DESCRIPTION

The following embodiments describe aspects of the present application in non-limiting detail below.

Figure 1:
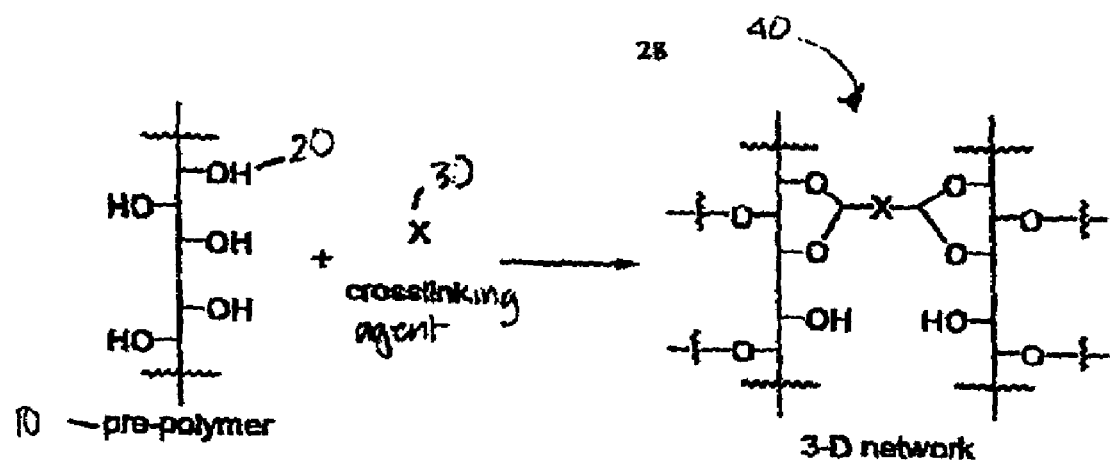
FIG. 1 is a diagram of the chemical reaction crosslinking a pre-polymer and a polyfunctional crosslinking agent to form a polymeric membrane.

FIG. 1 refers to one embodiment of a polymeric membrane made according to the present inventions. Pre-polymer 10 contains a plurality of crosslinkable moieties 20. A polyfunctional crosslinking agent 30 reacts with crosslinkable moieties 20 to form polymeric membrane 40. Preferably, the product of the crosslinking reaction is chemically stable under electrophoretic conditions.

Pre-polymer 10 may be formed from a homopolymer or a copolymer. In one embodiment, pre-polymer 10 is substantially devoid of charge, or has very limited charge. A pre-polymer is substantially devoid of charge or has very limited charge when condensation of pre-polymer 10 does not give rise to a significant degree of charged groups on the membrane after polymerization. In another embodiment, pre-polymer 10 is hydrophilic and has good water solubility. Preferably, the molecular weight range of pre-polymer 10 is in the range of about 10,000 to 200,000. More preferably, pre-polymer 10 has a molecular weight in the range of about 20,000 to 30,000. Preferably, the percentage of pre-polymer in the membrane is in the range of about 5 to 40% w/w, and more preferably about 5 to 20% w/w.

Pre-polymer 10 may be a natural or synthetic polymer. Synthetic pre-polymer may be formed by chain growth polymerization and/or by condensation polymerization. Control of the polymer gel network architecture may be influenced by the selection of pre-polymer 10. In some embodiments, synthetic pre-polymer 10 exhibits greater control over the nature of the polymer gel architecture. Synthetically produced polymers are often more chemically inert and can readily be made to exacting specifications, including molecular weight, degree of branching and charge groups present. Examples of synthetic pre-polymers include, but are not limited to, poly(vinyl alcohol) (PVAl), poly(vinyl amine), poly(ethylenimine), partially esterified poly(vinyl alcohols), copolymers of poly(vinyl alcohols), polymers of hydroxyethylmethacrylate and hydroxyethylacrylate, and glycidylacrylate and glycidylmethacrylate and various copolymers thereof.

Although the presence of charged residues in some natural pre-polymers result in a negative charge on the surface of these pre-polymers (and therefore often exhibit undesirable electroendosmotic properties when exposed to an electric field), natural pre-polymers are still suitable pre-polymers. Examples of suitable natural pre-polymers include, but are not limited to, starch, dextrans, cellulose derivatives, agarose, modified agaroses and other polysaccharides, as well as other natural pre-polymers having sufficient. Practitioners skilled in the art will appreciate that other natural pre-polymers 10 having crosslinkable moieties 20 suitable for crosslinking with polyfunctional crosslinking agent 30 may also be used.

Crosslinkable moieties 20 are arranged on pre-polymer 10 such that they may react with polyfunctional crosslinking agent 30 in order to form a chemical bond. Suitable chemistries and geometries to effect such a bond are well known in the art. In one embodiment, crosslinkable moieties 20 are hydroxyl groups. Other typical crosslinkable moieties 20 are amines. However, practitioners in the art will appreciate that other chemical substituents that crosslink with polyfunctional crosslinking agent 30 may also be used.

Polyfunctional crosslinking agent 30 has at least 2 functional groups that react with crosslinkable moieties 20 to form covalent bonds. In one embodiment, polyfunctional crosslinking agent 30 is itself uncharged. In another embodiment, polyfunctional crosslinking agent 30 does not contain a charged group. Such uncharged polyfunctional crosslinking agents 30 often do not give rise to charged groups via side reactions. In another embodiment, polyfunctional crosslinking agent 30 is hydrophilic. Preferably, any decomposition of the polyfunctional crosslinking agent will not lead to the significant development of charged groups within the polymeric matrix. The reactive groups in the polyfunctional crosslinking agent can be chemically equivalent or they may be of different chemical reactivity. For example, suitable polyfunctional crosslinking agents 30 include, but are not limited to, dialdehydes, such as glutaraldehyde, preferably of controlled chain length; di-isocyanates, such as $C_2$–$C_4$-alkylene di-isocyanates, e.g., ethylene di-isocyante; diacids, such as maleic or oxalic; water soluble epoxides; diesters; diacid halides; free or etherified N-methylol ureas or N-Methylol melamines, such as N,N-dimethyolurea, N,N-dimethyolurea dimethyl ether or trimethyolmelamine dimethyl ether; dihalogen compounds, or epichlorhydrin, dianhydrides, dicarboxylic acids, citric acid, dicarboxylic, olefin dialdehydes (e.g., propanedialdehyde), phthalaldehyde, 1,3-dichloroacetone and 1,3-dichloroisopropanol and molecules containing activated double bonds such as divinyl sulfone.

In one embodiment of polymeric membrane 40, polyfunctional crosslinking agent 30 is a dialdehyde. Non-limiting examples of suitable dialdehydes include glutaraldehyde, 2-hydroxyhexanedial-1,6, malonic dialdehyde, succinic dialdehyde and hexanedial-1,6. Most preferably, the polyfunctional crosslinking agent is glutaraldehyde. In another embodiment, polymeric membrane 40 is formed from pre-polymer poly(vinyl alcohol) crosslinked with glutaraldehyde.

In one embodiment, polymeric membrane 40 is a hydrogel. Polymeric membrane 40 may be self-supporting or it may be supported by one or more substrates. The substrate may be formed from any material that is conventionally used as a membrane support. In one embodiment, the substrate may be formed from a material that is chemically inert under electrophoretic conditions. In another embodiment, the substrate has good wet strength. Another desirable property is that the substrate does not substantially bind to the substance undergoing separation (e.g., proteins). The substrate may also be woven or non-woven material or a textile. The substrate may be in the form of a sheet, web, or any other appropriate form known in the art. Polymer membrane 40 may form on a surface of the substrate or the substrate may be within polymer membrane, e.g., the substrate may support polymer membrane 40 within a gel. Non-limiting examples of suitable materials for use as substrates include, but are not limited to polyvinyl alcohol, polyethyleneteraphthalate (PET), nylon and fibreglass, cellulose, cellulose derivatives, or any other suitable substrates known in the art.

For example heat bonded PET is a suitable substrate. Because of its hydrophobic nature, PET may require some pre-treatment to enable better wetting of the surface by the aqueous monomer solution. The surface may be pre-treated with a non-ionic surfactant, which renders the PET more hydrophilic while not introducing any charged groups into the system. However, in other substrates, no pre-treatment is necessary and simplifies membrane production.

Preferably, the substrate is hydrophilic in aqueous solvent systems. For example, polyvinyl alcohol paper is a suitable hydrophilic substrate. Available in several different weights and thicknesses, it may be used without pre-treatment. Another example of a suitable substrate is Papylon™, the trade name for the PVAl paper (Sansho Corporation, The $2^{nd}$ Kitahama Building 1-29, Kitaham-Higashi, Chuoh-Ku, Osaka, Japan, Ph: 06 6941 7895). Papylon™ has both excellent wet and dry strengths and has a very regular flat structure.

When crosslinkable moieties 20 are hydroxyl groups, a hydroxyl coordinating agent can be used to further decrease the functional pore size of the formed polymeric membrane in use during electrophoresis, thus providing further flexibility in achieving a desired pore size for the membrane. In one embodiment, the coordinating agent is a buffer. In another embodiment, the coordinating agent is borate. As another example, borate may be in the form of a buffer.

The coordinating agent may be used to control electrophoretic transfer or the rate of endosmosis. Without limiting the inventions as described herein and in the claims, it is believed that in one embodiment borate in the buffer reacts with water to form an anionic borate ion with a negative charge. Anionic borate is known to interact with 1,2- 1,3- and 1,4-diols to form negatively charged complexes. The complex formed between borate ions and PVAl induces an overall negative charge on the membrane surface, resulting in a net flux of buffer ions from stream 2 to stream 1. When the coordinating agent is a buffer, the pH of the buffer may be selected to be within a particular range. The polymer-buffer interaction may be used to alter electroendosmotic flow, e.g., borate buffers of different concentrations between pH 7 and 9, to concentrate biomacromolecules such as DNA, RNA and proteins. And thus, one embodiment treats polymeric membrane 40 with a coordinating agent that coordinates with crosslinkable moiety 20.

In another embodiment, addition of a hydrogen bond breaker in combination with the coordinating agent exerts further control over the electroendosmotic flow. The term "hydrogen bond breaker" is used herein to denote any chemical species that is capable of altering, modifying, controlling and or improving the hydrogen bonding characteristics of the pre-polymer component. As a non-limiting example, it has been postulated that the addition of a hydrogen bond breaker disrupts the existing intermolecular and intramolecular hydrogen bonding of crosslinkable moieties 20, e.g., hydroxyl groups, of pre-polymer 10. This allows for enhanced interaction between the hydroxyls and a charged coordinating agent, such as the borate ion. The hydrogen bond breaker is preferably chosen from urea, formamide, melamine, guanidine, potassium acetate or derivatives thereof. Other hydrogen bond breakers will be known to those skilled in the art. In one embodiment, the hydrogen bond breaker is urea.

The terms electroendosmosis or electroendosmotic property denote the bulk fluid flow through membranes caused by the presence or acquisition of an electrical charge. A charged membrane will tend to respond to the application of an external electric field, but because it is not free to move with respect to the electrolyte solution (buffer), there will be a movement of the electrolyte through the membrane. For example, a negatively charged membrane will cause solution to migrate towards the negative electrode under the influence of a potential difference. While there are techniques available to limit the amount of charged species present, they can increase the cost of the polymer. Additionally, depending on the properties of the buffer solution, it is often possible for the membranes to develop a partial charge by the absorption of ions during the electrophoresis. Advantageously, some embodiments of the present application exploit these processes to control the flow of buffer through the membranes.

Figure 2:
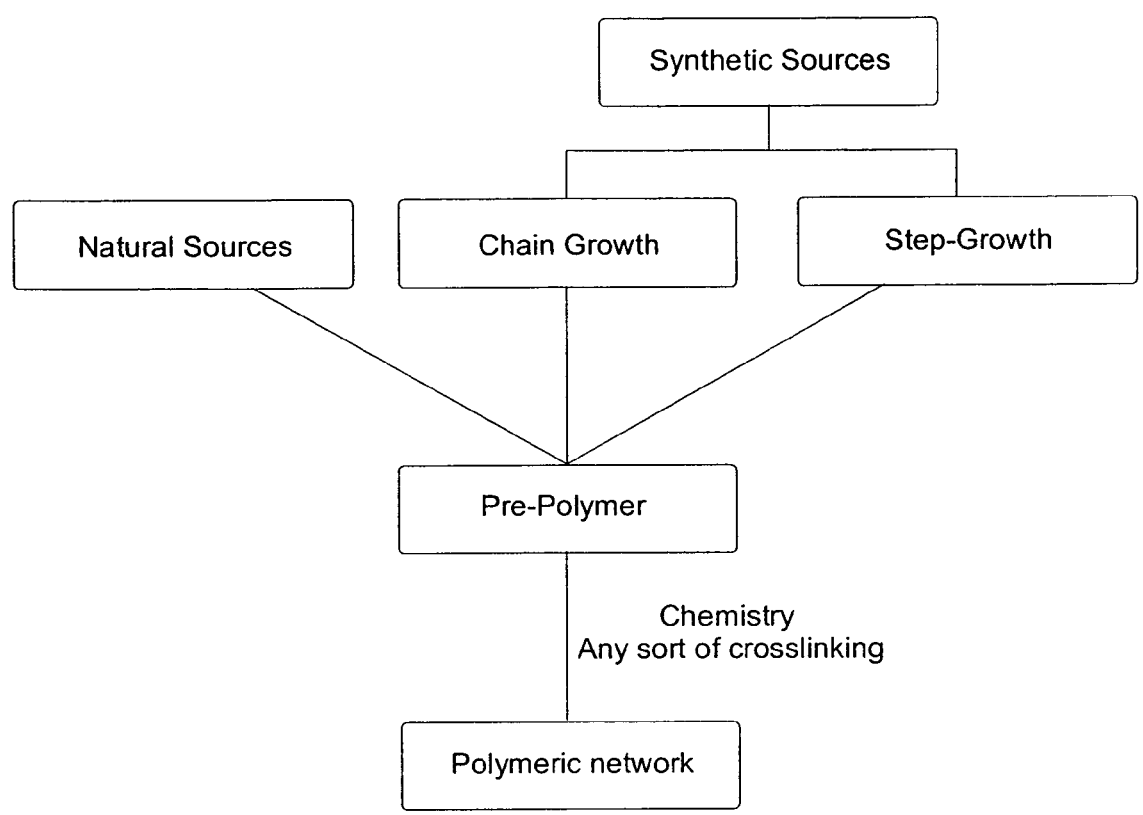
FIG. 2 is a schematic diagram of a method of forming a polymeric membrane.

FIG. 2 refers to a method of forming a polymeric membrane 40 by providing pre-polymer 10 having a plurality of crosslinkable moieties 20 and contacting pre-polymer 10 with a polyfunctional crosslinking agent 30 under conditions to form the polymeric membrane 40.

For example, these conditions include reacting crosslinkable moieties 20 with polyfunctional crosslinking agent 30 via a variety of condensation chemistries to form extended polymeric matrices. Unlike conventional free radical systems, where the crosslinked membrane is formed entirely by chain growth, embodiments described herein may be formed by a step-growth reaction with a polyfunctional crosslinking agent 30. This step-growth approach to forming a polymeric network allows for greater control over the properties of the polymeric network. The term "step-growth" (condensation growth) denotes the build-up of a polymer network by gradual or stepwise growth with time. A consequence of these individual step reactions is that the network can be built up in a controlled fashion. However, as noted above, synthetic pre-polymer may be formed via a chain growth process or a step growth process 80. Pre-polymer 10 may also be formed form natural sources 50 or synthetic sources 70.

In one embodiment, pre-polymer 10 is a polyol. For example, poly(vinyl alcohol) (PVAl) is a suitable pre-polymer. PVAl may be prepared by the hydrolysis of poly(vinyl acetate) (PVAc), which is synthesized via the free radical chain polymerization of vinyl acetate. The level of hydrolysis is easily controlled, giving polymers with varying amounts of free hydroxyls. The molecular weight of the polymer can also be controlled during the polymerization of the vinyl acetate monomer.

Other suitable crosslinking conditions include, for example, acetalization, etherification or esterification. In one embodiment, the crosslinking reaction is carried out under conditions such that the resultant crosslinked product is in the form of a hydrogel. Preferably, the crosslinking reaction is performed under atmospheric pressure at a temperature in the range of about 10 to 60° C., more preferably about 20 to 40° C. Preferably, the crosslinking reaction is carried out under atmospheric pressure and room temperature. Under some suitable conditions, a catalyst may be used. Acid, base, or any other suitable catalyst known in the art may catalyze the crosslinking reaction. Further control over the rate of crosslinking reactions can be exerted via adjustment of the concentration of catalyst added.

Figure 3:
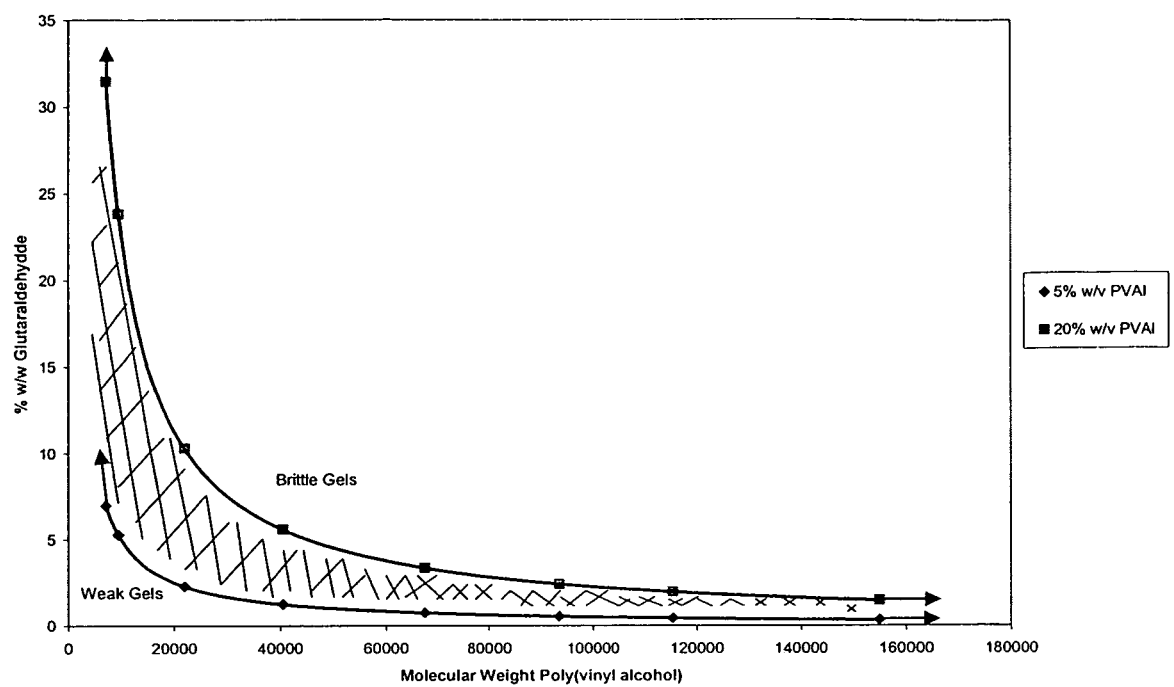
FIG. 3 is a graph illustrating the relationship between the molecular weight of pre-polymer polyol and the percentage weight (w/w) of the polyfunctional crosslinking agent added.

The membrane network properties can be manipulated by controlling the ratio of pre-polymer 10 to polyfunctional crosslinking agent 30. The properties of the network depend on both the amount of polyfunctional crosslinking agent 30 (e.g., glutaraldehyde) and on the molecular weight of pre-polymer 10. While not limiting the inventions described and claimed herein, it is expected that there is a connection between the molecular weight of pre-polymer 10 and the amount of polyfunctional crosslinking agent 30 needed. FIG. 3 illustrates the relationship between the molecular weight of pre-polymer 10 poly(vinyl alcohol) and the quantity of polyfunctional crosslinking agent 30 glutaraldehyde used.

Embodiments of the present method demonstrate that control of the ratio between PVAl and the polyfunctional crosslinking agent, glutaraldehyde, result in control over the properties of the network, including mechanical strength, porosity, opacity, etc. By control and selection of the ratio of polyfunctional crosslinking agent to polymer, the present method produces polymeric membranes with desirable pore sizes.

In another embodiment, purification of commercial grade glutaraldehyde results in charged group residues being removed, thereby enhancing the properties of the thus formed crosslinked products. In addition, purification of commercial grade glutaraldehyde limits the amount of dimers and higher aldehyde oligomers present in the crosslinking solution. Commercial grade glutaraldehyde often contains a certain amount of oligomeric entities. By careful manipulation of the purification process, the present method exerts more control over the polymer network structure.

FIG. 3 demonstrates that the lower the molecular weight of pre-polymer 10, the more polyfunctional crosslinking agent 30 that is required to obtain an equivalent network formation. While not limiting the inventions described and claimed herein, , the relationship between pre-polymer molecular weight and concentration of polyfunctional crosslinking agent is given by the FIG. 3. The preferred percentage weight range of polyfunctional crosslinking agent 30 in polymeric membrane 40 is between about 1% and 20% w/w, more preferably between about 4% to 15%, and most preferably, about 4.5% to 9.2% w/w. In some embodiments, higher concentrations of polyfunctional crosslinking agent 30 may be desirable in the range of about 100% to 500% w/w excess in relation to polymer.

Increasing the concentration of pre-polymer in the membrane may reduce the rate of electroendosmosis. Even in combination with complexing buffers as coordinating agents, higher concentrations of polymer leads to marked reductions in bulk flow of buffer. While not limiting the inventions as described and claimed herein, it is believed that the higher concentrations of pre-polymer (for example PVA1), can lead to larger crystalline domains, which interfere with the association of the buffers on the membrane, thus reducing the observed endosmosis effects.

As shown in Table 1, the various effects of buffer choice and polymer concentration are presented.

TABLE 1

Examples of membrane formulations and characteristics

| Formulation[a] | Buffer[b] | Flow Rate (mL min$^{-1}$) | Estimated Pore Size (PS) (kDa) | Notes[c] |
|---|---|---|---|---|
| 5/4.5 | P | 0.04 | 67 < PS | Transfer slow |
| 5/4.5 | MBT | 0.025 | 67 < PS < 340 | purified glutaraldehyde |
| 5/4.5 | TG | 0.13 | 67 < PS < 340 | |
| 5/4.5 | TG | 0.025 | 67 < PS < 340 | purified glutaraldehyde |
| 5/4.5 | TG | 0.10 | 67 < PS < 340 | PVA1 substrate |
| 5/4.5 | TG | 1.50 | 67 < PS | TB added |
| 5/6.8 | TG | 0.40 | 67 < PS | |
| 5/4.5 | TG | 0.23 | | 13–23 k PVA1 |
| 5/4.5 | TG | 0.20 | | 13–23 k 89% H. |
| 5/4.5 | TG | 0.12 | 67 < PS | 89–98 k PVA1 |
| 5/4.5 | TG | 0.25 | 67 < PS | 124–186 k PVA1 |
| 5/0.65 | TG | 0.20 | 67 < PS | 124–186 k PVA1 |
| 5/0.96 | TG | 0.18 | | 89–98 k PVA1 |
| 10/2.29 | TG | 0.13 | | |
| 10/2.29 | TG | 0.23 | | 13–23 k PVA1 |
| 10/2.29 | TG | 0.20 | | 13–23 k PVA1 89% H. |
| 20/9.2 | TG | 0.06 | 67 < PS < 340 | |
| 5/4.5 | TB | 1.40 | PS < 340 | |
| 5/4.5 | TB | 0.31 | PS < 340 | NaCl added |
| 5/4.5 | TB | 2.82 | | Urea added |
| 5/4.5 | TB | 0.09 | | 3 membrane |
| 5/0.65 | TB | 1.80 | 67 < PS | 124–186 k PVA1 |
| 10/2.29 | TB | 0.40 | | |
| 10/2.29 | TB | 0.38 | | 13–23 k PVA1 |
| 10/2.29 | TB | 0.40 | | 13–23 k PVA1 89% H. |
| 10/4.5 | TB | 0.35 | | |
| 20/9.2 | TB | 0.04 | no transfer | tight matrix |

[a]% PVA1 (w/v)/Glutaraldehyde (w/w)
[b]TG = Tris-Glycine,
P = Phosphate,
TB = Tris-Borate,
MBT = Mes-BisTris
[c]22 K MWt PVA1 used unless otherwise stated Another aspect provides a method of separating molecules by providing polymeric membrane 40 formed by reacting a pre-polymer 10 having crosslinkable moieties 20 with a polyfunctional crosslinking agent 30 and subjecting polymeric membrane 40 and a sample to be separated to a separation technique so as to separate the molecules. For example, this method may be used for separating charged species, or species capable of bearing a charge such as a biomolecule. In one embodiment, the bio-molecules may be proteins, peptides, DNA or RNA.

In another example, the separation technique may be an electrophoretic technique. This technique allows for the separation of molecules on the basis of size or charge under native conditions. The electrophoretic technique may be that disclosed in U.S. Pat. No. 5,650,055, the entire disclosure of which is incorporated herein by reference.

In another embodiment, the separation technique may include the use of borate in solution to concentrate protein samples electrophoretically to control protein transfer when using, for example, a membrane arrangement involving one or moremembranes in accordance with the application located between restriction membranes. Control over rate of protein transfer by the addition of neutral salts may also be used when using such a 3-membrane arrangement.

Another aspect provides a device comprising at least one membrane in accordance with the present invention located between two restriction membranes.

Certain aspects of the polymeric membrane are particularly suitable for use in electrophoretic separation techniques. Accordingly, another aspect provides an electrophoretic medium for use in an electrophoretic technique, the electrophoretic medium comprising a polymeric membrane 40 formed from a pre-polymer 10 having a plurality of crosslinkable moieties 20, the crosslinkable moieties being crosslinked with a polyfunctional crosslinking agent 30. For example, the electrophoretic medium may be enclosed in a cartridge suitable for use in an electrophoretic device, the cartridge incorporating a polymeric membrane 40. The cartridge may be any suitable cartridge known to those skilled in the art. For example, the cartridge may be that described in U.S. Pat. Nos. 5,650,055, 5,039,386 and WO 0013776, the disclosures of which are incorporated herein in their entirety.

To assist in understanding the embodiments and aspects illustrated above, the following examples are included and describe the results of a series of experiments. The following examples relating to this invention should not be construed to specifically limit the invention or such variations of the invention, now known or later developed, which fall within the scope of the invention as described and claimed herein.

MEMBRANE PREPARATION

Pre-treatment of Membrane Substrate

Unwoven poly(ethyleneterephthalate) (PET) sheets that served as a mechanical support were treated with aqueous solution of Teric BL8 (0.5% (v/v), Huntsman Corp. Australia) a non-ionic surfactant was used to improve surface wettability. The sheets were cut to 18 cm×8 cm and placed on a glass sheet to cast the gel membranes.

EXAMPLE 1

Preparation of 5% PVA1 Membrane Crosslinked with Glutaraldehyde at 4.5% (w/w).

A solution of PVA1 (5% w/v, 10 mL MW 22,000, 97.5%–99.5% hydrolyzed) and 0.2 M HCl (0.333 µL 6.0 M solution) was prepared. To this, glutaraldehyde (91.5 µL 25% w/v in aqueous solution) was then added. The solution was poured across the treated PET support and allowed to stand at room temperature for 30 min. Membranes were then washed in excess distilled water to remove residual catalyst prior to use.

EXAMPLE 2

Preparation of 5% PVAl Membrane Crosslinked with Glutaraldehyde at 6.8% (w/w).

A solution of PVAl (5% w/v, 10 mL MW 22,000, 97.5%–99.5% hydrolyzed) and 0.2 M HCl (0.333 μL 6.0 M solution) was prepared. To this glutaraldehyde (136.5 μL 25% w/v in aqueous solution) was then added. The solution was poured across the treated PET support and allowed to stand at room temperature for 30 min. Membranes were then washed in excess distilled water to remove residual catalyst prior to use.

EXAMPLE 3

Preparation of 20% PVAl Membrane Crosslinked with Glutaraldehyde at 9.2% (w/w).

A solution of PVAl (20% w/v, 10 mL MW 22,000, 97.5%–99.5% hydrolyzed) and 0.05 M HCl (0.083 μL 6.0 M) was prepared. To this glutaraldehyde (732 μL 25% w/v in aqueous solution) was then added. The solution was poured across the treated PET support and allowed to stand at room temperature for 30 min. Membranes were then washed in excess distilled water to remove residual catalyst prior to use.

EXAMPLE 4

Preparation of 5% PVAl Membrane Crosslinked with Glutaraldehyde at 1.08% (w/w).

A solution of PVAl (5% w/v, 10 mL, MW 89,000–98,000, 99+% hydrolysed) and 0.2 M HCl (0.333 μL 6.0 M solution) was prepared. To this glutaraldehyde (21.53 μL 25% w/v in aqueous solution) was then added. The solution was poured across the treated PET support and allowed to stand at room temperature for 30 min. Membranes were then washed in excess distilled water to remove residual catalyst prior to use.

EXAMPLE 5

Preparation of 5% PVAl Membrane Crosslinked with Glutaraldehyde at 4.5% (w/w).

A solution of PVAl (5% w/v, 10 mL, MW 89,000–98,000, 99+% hydrolysed) and 0.2 M HCl (0.333 μL 6.0 M solution) was prepared. To this glutaraldehyde (91.5 μL 25% w/v in aqueous solution) was then added. The solution was poured across the treated PET support and allowed to stand at room temperature for 30 min. Membranes were then washed in excess distilled water to remove residual catalyst prior to use.

EXAMPLE 6

Preparation of 5% PVAl Membrane Crosslinked with Glutaraldehyde at 0.65% (w/w).

A solution of PVAl (5% w/v, 10 mL, MW 124,000–186,000, 99+% hydrolysed) and 0.2 M HCl (0.333 μL 6.0 M solution) was prepared. To this glutaraldehyde (12.98 μL 25% w/v in aqueous solution) was then added. The solution was poured across the treated PET support and allowed to stand at room temperature for 30 min. Membranes were then washed in excess distilled water to remove residual catalyst prior to use.

EXAMPLE 7

Preparation of 5% PVAl Membrane Crosslinked with Glutaraldehyde at 4.5% (w/w).

A solution of PVAl (5% w/v, 10 mL, MW 124,000–186,000, 99+% hydrolysed) and 0.2 M HCl (0.333 μL 6.0 M solution) was prepared. To this glutaraldehyde (91.5 μL 25% w/v in aqueous solution) was then added. The solution was poured across the treated PET support and allowed to stand at room temperature for 30 min. Membranes were then washed in excess distilled water to remove residual catalyst prior to use.

EXAMPLE 8

Preparation of 20% PVAl Membrane Crosslinked with Glutaraldehyde at 9.2% (w/w) on PVAl Paper.

A solution of PVAl (20% w/v, 10 mL, 22,000, 97.5%–99.5% hydrolysed) and 0.05 M HCl (0.083 μL 6.0 M solution) was prepared. To this glutaraldehyde (732 μL 25% w/v in aqueous solution) was then added. The solution was poured across an untreated PVAl paper support and allowed to stand at room temperature for 30 min. Membranes were then washed in excess distilled water to remove residual catalyst prior to use.

EXAMPLE 9

Preparation of 5% PVAl Membrane Crosslinked with Freshly Distilled Glutaraldehyde at 4.5% (w/w).

A solution of PVAl (5% w/v, 10 mL MW 22,000, 97.5%–99.5% hydrolyzed) and 0.2 M HCl (0.333 μL 6.0 M solution) was prepared. To this, freshly distilled glutaraldehyde (91.5 μL 25% w/v in aqueous solution) was then added. The solution was poured across the treated PET support and allowed to stand at room temperature for 30 min. Membranes were then washed in excess distilled water to remove residual catalyst prior to use.

EXAMPLE 10

Preparation of 5% PVAl Membrane Crosslinked with Divinyl Sulfone at 54% (w/w).

A solution of PVAl (5% w/v, 10 mL MW 22,000, 97.5%–99.5% hydrolyzed) and 0.5 M NaOH (0.2 g) was prepared. To this, divinyl sulfone (317 μL) was then added. The solution was poured across the treated PET support and allowed to stand at room temperature for 30 min. Membranes were then washed in excess distilled water to remove residual catalyst prior to use.

EXAMPLE 11

Preparation of 5% PVAl Membrane Crosslinked with Divinyl Sulfone at 40% (w/w).

A solution of PVAl (5% w/v, 10 mL MW 22,000, 97.5%–99.5% hydrolyzed) and 0.5 M NaOH (0.2 g) was prepared. To this, divinyl sulfone (238 μL) was then added. The solution was poured across the treated PET support and allowed to stand at room temperature for 30 min. Membranes were then washed in excess distilled water to remove residual catalyst prior to use.

EXAMPLE 12

Preparation of 5% PVAl Membrane Crosslinked with Divinyl Sulfone at 27% (w/w).

A solution of PVAl (5% w/v, 10 mL MW 22,000, 97.5%–99.5% hydrolyzed) and 0.5 M NaOH (0.2 g) was prepared. To this, divinyl sulfone (159 µL) was then added. The solution was poured across the treated PET support and allowed to stand at room temperature for 30 min. Membranes were then washed in excess distilled water to remove residual catalyst prior to use.

EXAMPLE 13

Preparation of 5% PVAl Membrane Crosslinked with Divinyl Sulfone at 21% (w/w).

A solution of PVAl (5% w/v, 10 mL MW 22,000, 97.5%–99.5% hydrolyzed) and 0.5 M NaOH (0.2 g) was prepared. To this, divinyl sulfone (127 µL) was then added. The solution was poured across the treated PET support and allowed to stand at room temperature for 30 min. Membranes were then washed in excess distilled water to remove residual catalyst prior to use.

EXAMPLE 14

Preparation of 5% PVAl Membrane Crosslinked with Ethyleneglycol Diglycidyl Ether at 633% (w/w).

A solution of PVAl (5% w/v, 10 mL MW 22,000, 97.5%–99.5% hydrolyzed) and 0.5 M NaOH (0.2 g) was prepared. To this, ethyleneglycol diglycidyl ether (5664 µL, 50% solution) was then added. The solution was poured across the treated PET support and allowed to stand at 60° C. for 24 hrs. Membranes were then washed in excess distilled water to remove residual catalyst prior to use.

EXAMPLE 15

Preparation of 5% PVAl Membrane Crosslinked with 1,4-butanediol Diglycidyl Ether at 1126% (w/w).

A solution of PVAl (5% w/v, 10 mL MW 22,000, 97.5%–99.5% hydrolyzed) and 0.5 M NaOH (0.2 g) was prepared. To this, 1,4-butanediol diglycidyl ether (5533 µL, 97% solution) was then added. The solution was poured across the treated PET support and allowed to stand at 60° C. for 24 hrs. Membranes were then washed in excess distilled water to remove residual catalyst prior to use.

ELECTROPHORESIS MEMBRANE CONFIGURATIONS

Electrophoresis Apparatus

A membrane-based electrophoresis apparatus used to test the membranes according to the present application was produced by Gradipore Limited and called a Gradiflow™ unit or apparatus. The unit or apparatus comprised:

(a) a cathode in a cathode compartment;
(b) an anode in an anode compartment, the anode disposed relative to the cathode so as to be adapted to generate an electric field in an electric field area there between upon application of an electric potential between the cathode and the anode;
(c) a first membrane disposed in the electric field area;
(d) a second membrane disposed between cathode compartment and the first membrane so as to define a first interstitial volume (stream 1) therebetween;
(e) a third membrane disposed between anode compartment and the first membrane so as to define a second interstitial volume (stream 2) therebetween;
(f) electrode buffer reservoir in fluid communication with the cathode chamber and the anode chamber;
(g) stream 1 reservoir in fluid communication with the first interstitial volume (stream 1);
(h) stream 2 reservoir in fluid communication with the second interstitial volume (stream 2);
(i) means adapted to provide buffer or solvent to the cathode compartment and the anode compartment from the electrode buffer reservoir;
(j) means adapted to provide sample or buffer to the second interstitial volume (stream 2) from the stream 2 reservoir;
(k) cooling means for the electrode buffer adapted for removing heat generated in the apparatus; and
(l) means adapted to provide a sample constituent to the first interstitial volume from the stream 1 reservoir, wherein upon application of the electric potential, a component is removed from the sample constituent through at least one membrane and provided to the other of the second interstitial volumes or to the cathode or anode chambers.

The cathode chamber and the anode chamber are supplied with suitable solvent or buffer solutions by any suitable pumping means. A sample to be tested was usually supplied to the first interstitial volume from the sample chamber by a pumping means.

The electrode chambers and the interstitial volumes were configured to allow flow of the respective fluid/buffer and sample solutions forming streams. In this form, large volumes can be processed quickly and efficiently. The solutions were typically moved or recirculated through the chambers and volumes from respective reservoirs by peristaltic pumps.

The second and third membranes were typically restriction membranes having a molecular weight cut-off less than that of the first membrane (called the separation membrane).

In use, a sample was placed in the first interstitial volume (stream 1), buffer or solvent was provided to the electrode chambers and the second interstitial volume (stream 2), an electric potential was applied to the electric field area causing at least one constituent in the sample to move to buffer/solvent in the cathode chamber or buffer/solvent in the second interstitial volume.

For convenience, the first interstitial volume or stream is called the stream 1 and the second interstitial volume or stream is called the stream 2. Typically, sample was placed in stream 1 and constituents caused to move through the separation membrane into stream 2.

The apparatus contained a cartridge that housed the three membranes and forming stream 1 and stream 2.

Cartridge Format 1

Figure 4:
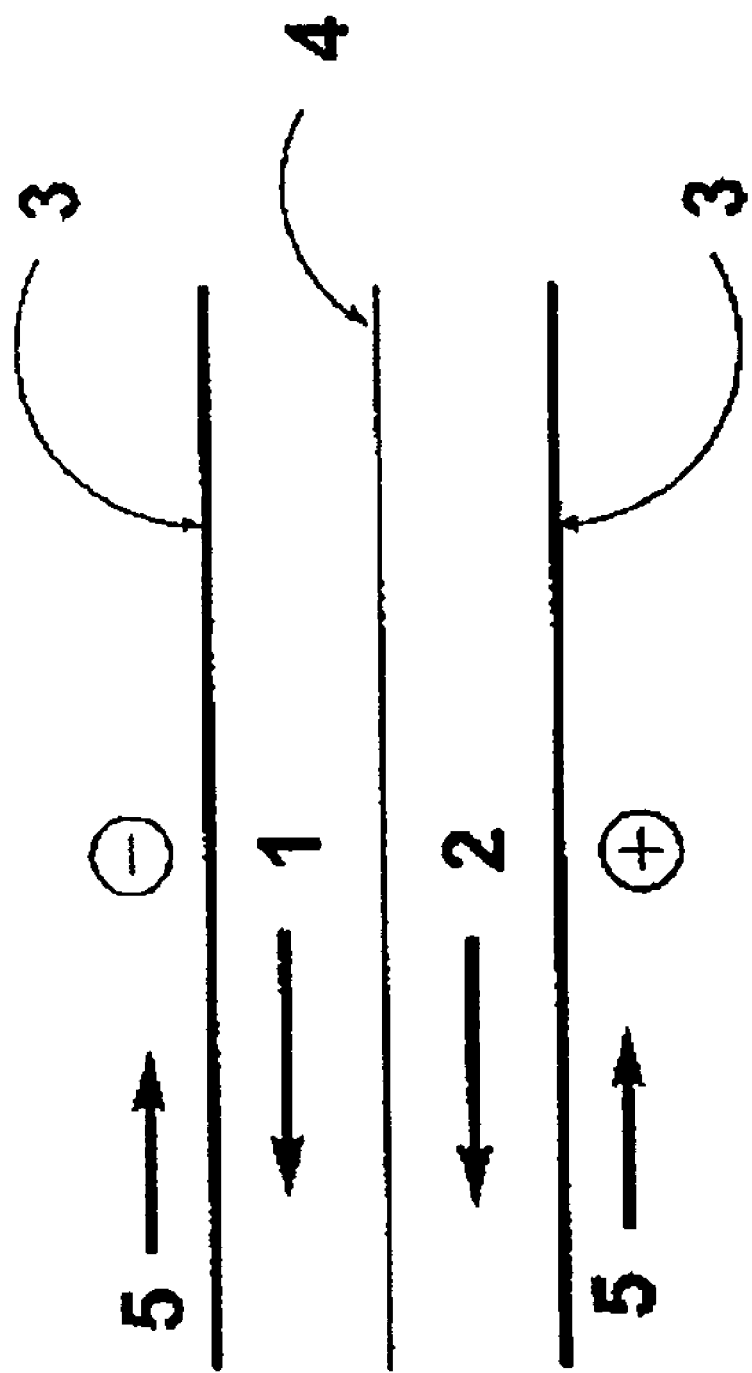
FIG. 4 is a schematic representation of a typical three-membrane arrangement, where (1) stream 1, (2) stream 2, (3) restriction membrane, (4) separation membrane, and (5) cooling/electrophoresis buffer.

For each electroendosmosis and protein separation test performed, a separating cartridge was assembled as per FIG. 4. PAAm restriction membranes were used to prevent protein transfer from stream 1 and anodic stream to the cooling/electrophoresis buffer. Each PVAl membrane was used as a separation membrane between the restriction membranes. This system was used unless otherwise stated. The electrophoretic conditions associated with cartridge format 1 are more fully described in U.S. Pat. Nos. 5,650,055, 5,039,386 and WO 0013776.

Cartridge Format 2

Figure 5:
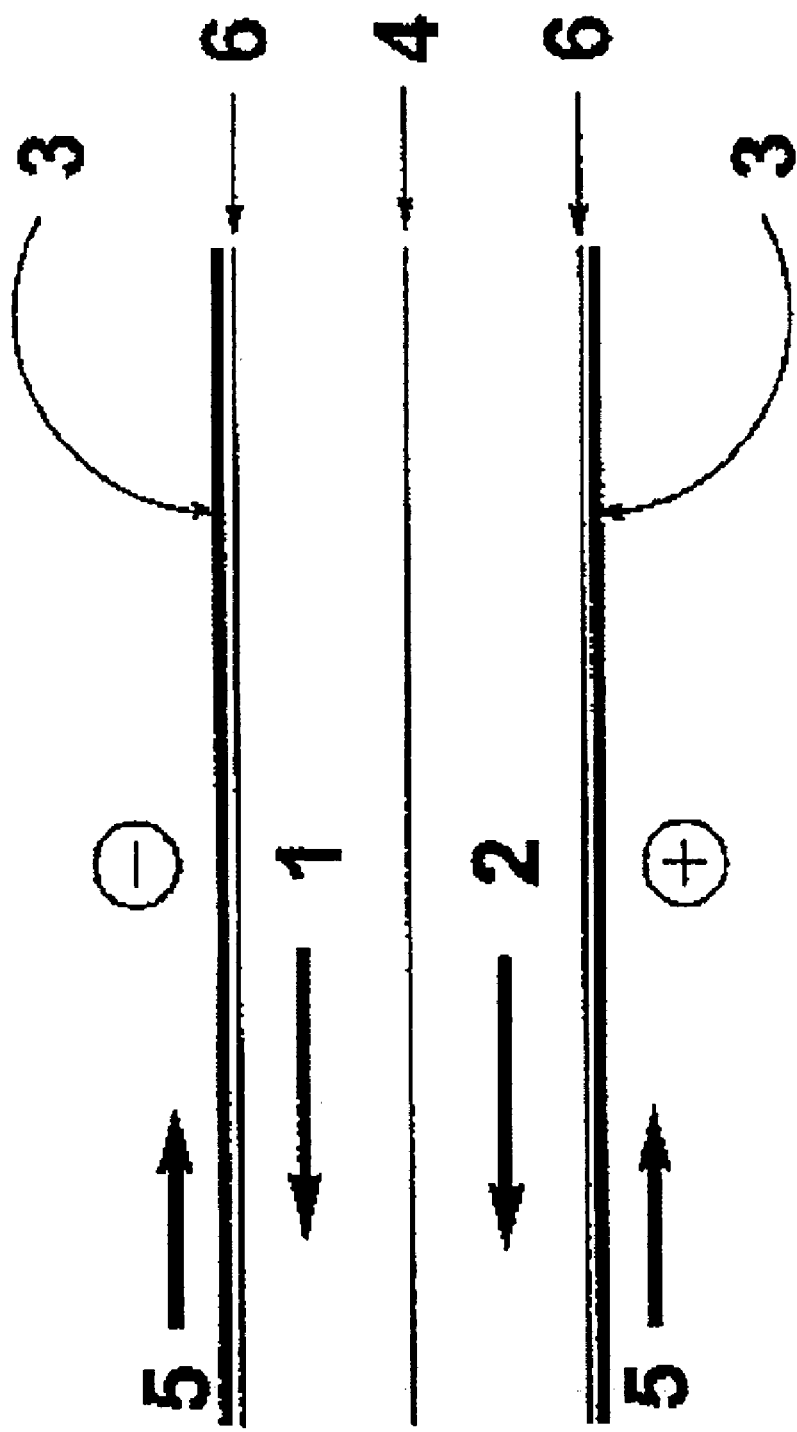
FIG. 5 is a schematic representation of a three-membrane arrangement including a polymeric membrane according to the present application, where (1) stream 1, (2) stream 2, (3) restriction membrane, (4) separation membrane, (5) cooling/electrophoresis buffer, and (6) an embodiment of the present polymeric membrane.

An alternative membrane cartridge system was used to the above system in order to examine the effects on electroendosmosis and protein separation, FIG. 5. This comprised the same system as described above together with a crosslinked PVAM membrane, (marked 6, FIG. 5, placed adjacent to the restriction membranes. The electrophoretic conditions associated with cartridge two are analogous to the conditions described for cartridge format 1. The electrophoretic conditions associated with cartridge format 1 are more fully described in U.S. Pat. Nos. 5,650,055, 5,039,386 and WO 0013776.

Leak Testing

Before any protein separation or electroendosmosis tests were performed, it was necessary to ensure that the membranes used did not leak. A series of leak tests were used to ensure membrane and cartridge integrity.

An initial leak test was required to check the integrity of the membrane. Proteins to be separated according to their charge or size may leak through any holes if a membrane is not formed correctly. The peristaltic pump was switched on and any volume changes were recorded in the stream 1 and stream 2 at 1-minute intervals for 15 minutes. No volume change indicated that there was no leakage in the separation membranes tested.

The cooling and electrophoresis (electrode) buffer pump was then switched on together with the peristaltic pump to test the restriction membranes for leakage. Similarly to the initial leak test, no volume changes to the stream 1 and stream 2 indicated that these were not leaking.

Electroendosmosis Testing

Various buffers were used in the Gradiflow™ electrophoresis unit to determine the electroendosmotic rates through the membranes with the different levels of crosslinked PVAl membranes. Electroendosmosis manifests itself as a volume change in either the stream 1 or stream 2 reservoirs. Stream 1 is adjacent to the cathode compartment while stream 2 is adjacent to the anode compartment. Several common buffers, 40 mM Tris-Borate at pH 8.5, 40 mM Tris-Glycine at pH 9.0, and 40 mM Phosphate at pH 7.0 were used for these tests. With both of the electrode and sample pumps switched on, electroendosmotic testing was conducted under the influence of a power supply at 200 V, 500 mA for 20 minutes. Volume changes in the stream 1 and stream 2 reservoirs were monitored or calculated. Any change in volume over the 20 minute time period results from bulk fluid movement from any one or more of stream 1, stream 2, anode or cathode reservoirs. These readings were recorded at 1-minute intervals. The flow rate was calculated from the difference in volume between the initial stream 1 and final stream 1 reservoir divided by the time (i.e an increase of 4 mL in 20 minutes is a flow rate of 0.2 mL/min).

EXAMPLE 16

Electroendosmosis of 5% (w/v) PVAl Crosslinked Membranes with Glutaraldehyde at 4.5% (w/w) in 40 mM Tris-Glycine Buffer, pH 9.0.

Electroendosmosis testing using the Gradiflow™ unit showed a flow rate of 0.13 mL min$^{-1}$ from stream 1 reservoir to the stream 2 reservoir.

EXAMPLE 17

Electroendosmosis of 20% (w/v) PVAl Crosslinked Membranes with Glutaraldehyde at 9.2% (w/w) in 40 mM Tris-Glycine Buffer, pH 9.0.

Electroendosmosis testing using the Gradiflow™ unit showed a flow rate of 0.06 mL min$^{-1}$ from the anodic to the cathodic reservoir. There was also a marked increase in the conductivity of this solution. [

EXAMPLE 18

Electroendosmosis of 5% (w/v) PVAl Crosslinked Membranes with Glutaraldehyde at 4.5% (w/w) in 40 mM Tris-Borate Buffer, pH 8.5 with the Addition of NaCl (40 mM).

Electroendosmosis testing using 40 mM Tris-Borate buffer with 40 mM NaCl displayed a flow rate of 0.31 mL min$^{-1}$ from the stream 1 to the stream 2 reservoir. The addition of salt increased the conductivity of the buffer solution from 0.959 mS to 2.82 mS.

EXAMPLE 19

Electroendosmosis of 5% (w/v) PVAl Crosslinked Membranes with Glutaraldehyde at 4.5% (w/w) in 40 mM Tris-Glycine, pH 9.0 with the Substitution of Tris-Borate Buffer, pH 8.5.

To confirm the induced electroendosmosis of the borate ion on crosslinked PVAl membranes, the stream 2 Tris-Glycine buffer sample was replaced with Tris-Borate buffer. Electroendosmosis testing showed a flow rate of 1.5 mL min$^{-1}$ through the exchange of glycine for borate.

EXAMPLE 20

Electroendosmosis Rate Determination Using the Alternative "3-membrane" Cartridge Containing 5% (w/v) PVAl Crosslinked Membranes with Glutaraldehyde at 4.5% (w/w) in 40 mM Tris-Borate Buffer, pH 8.5.

Electroendosmosis testing showed a flow rate of 0.09 mL min$^{-1}$ from stream 1 to the stream 2 reservoir. The alternative membrane arrangement showed that volume increase in stream 1 was reduced. Similarly, the volume decrease from the stream 2 by electroendosmosis was compensated with buffer replacement from the cooling/electrophoresis buffer reservoir.

EXAMPLE 21

Electroendosmosis of 5% (w/v) PVAl Crosslinked Membranes with Glutaraldehyde at 4.5% (w/w) on PVAl paper in 40 mM Tris-Glycine Buffer, pH 9.0.

Electroendosmosis testing using the Gradiflow™ unit showed a flow rate of 0.10 mL min$^{-1}$ from the stream 2 to the stream 1 reservoir.

EXAMPLE 22

Electroendosmosis of 5% (w/v) PVAl Crosslinked Membranes with Glutaraldehyde at 4.5% (w/w) on PVAl Paper in 40 mM Tris-Borate Buffer, pH 8.5.

Electroendosmosis testing using the Gradiflow™ unit showed flow rate of 1.2 mL min$^{-1}$ from the stream 2 to the stream 1 reservoir.

EXAMPLE 23

Electroendosmosis of 5% (w/v) PVAl Crosslinked Membranes with Distilled Glutaraldehyde at 4.5% (w/w) on PVAl Paper in 40 mM Tris-Glycine Buffer, pH 9.0.

Electroendosmosis testing using the Gradiflow™ unit showed flow rate of 0.025 mL min$^{-1}$ from the stream 1 to the stream 2 reservoir.

EXAMPLE 24

Electroendosmosis of 5% (w/v) PVAl Crosslinked Membranes with Distilled Glutaraldehyde at 4.5% (w/w) on PVAl Paper in 40 mM Mes-BisTris Buffer, pH 6.85.

Electroendosmosis testing using the Gradiflow™ unit showed flow rate of 0.025 mL min$^{-1}$ from the stream 2 to the stream 1 reservoir.

EXAMPLE 25

Electroendosmosis of 5% (w/v) PVAl Crosslinked Membranes with Divinyl Sulfone at 45% (w/w) on PVAl Paper in 40 mM Mes-BisTris Buffer, pH 6.85.

Electroendosmosis testing using the Gradiflow™ unit showed flow rate of 0.9 mL min$^{-1}$ from the stream 2 to the stream 1 reservoir.

EXAMPLE 26

Electroendosmosis of 5% (w/v) PVAl Crosslinked Membranes with Divinyl Sulfone at 34% (w/w) on PVAl Paper in 40 mM Mes-BisTris Buffer, pH 6.85.

Electroendosmosis testing using the Gradiflow™ unit showed flow rate of 0.075 mL min$^{-1}$ from the stream 2 to the stream 1 reservoir.

EXAMPLE 27

Electroendosmosis of 5% (w/v) PVAl Crosslinked Membranes with Divinyl Sulfone at 23% (w/w) on PVAl Paper in 40 mM Mes-BisTris Buffer, pH 6.85.

Electroendosmosis testing using the Gradiflow™ unit showed flow rate of 0.043 mL min$^{-1}$ from the stream 2 to the stream 1 reservoir.

EXAMPLE 28

Electroendosmosis of 5% (w/v) PVAl Crosslinked Membranes with Divinyl Sulfone at 18% (w/w) on PVAl Paper in 40 mM Mes-BisTris Buffer, pH 6.85.

Electroendosmosis testing using the Gradiflow™ unit showed flow rate of 0.025 mL min$^{-1}$ from the stream 2 to the stream 1 reservoir.

ELECTROPHORESIS SEPARATIONS

Electrophoresis separations were conducted in a membrane-based electrophoresis apparatus described above under electrophoretic conditions set out below.

Protein separation was examined using various membranes and buffer systems as described above. Protein samples were used to conduct a protein transfer from stream 1 into stream 2 of a membrane-based electrophoresis separation apparatus produced by Gradipore Limited with suitable buffers. Bovine serum albumin (BSA, 67 kDa) and chicken egg ovalbumin (Ovalb, 45 kDa) samples prepared in 10 mL buffer used for separation, or 10 mL of human serum cryo-precipitate from plasma, containing a mixture of proteins including Fibrinogen (340 kDa) a large glycoprotein and smaller proteins such as human serum albumin (HSA, 67 kDa) and immunoglobulin G (IgG, between 47 and 56 kDa). The cryo-precipitate was diluted with 20 mL of buffer for separation. Protein solution was placed in stream 1 whilst stream 2 was filled with test buffer. Fractions (100 μL) were taken from stream 1 and stream 2 reservoirs at 10 minute intervals from time 0 up to 60 minutes and analysed by PAGE.

PAGE analysis of BSA/Ovalb protein mixture separations were performed under native conditions using 80 mM Tris-Borate buffer, pH 8.5 at 200 V, 500 mA for 90 minutes. For the cryo-precipitate, PAGE was performed under reducing conditions. Fractions (50 μL) were taken from stream 1 and stream 2 reservoirs at 10 minute intervals. These samples were reduced with 10 μL dithiothreitol (DTT) and separated by PAGE with SDS Tris-Glycine buffer, pH 8.5 at 150V, 500 mA for 90 minutes. The proteins were then stained with coomassie brilliant blue G-250 and washed with 10% acetic acid. The protein bands were then visualised in the gels.

EXAMPLE 29

Protein Separation Using 5% (w/v) PVAl Crosslinked Membranes with Glutaraldehyde at 6.8% (w/w) in 40 mM Tris-Glycine Buffer, pH 9.0.

Figure 6:
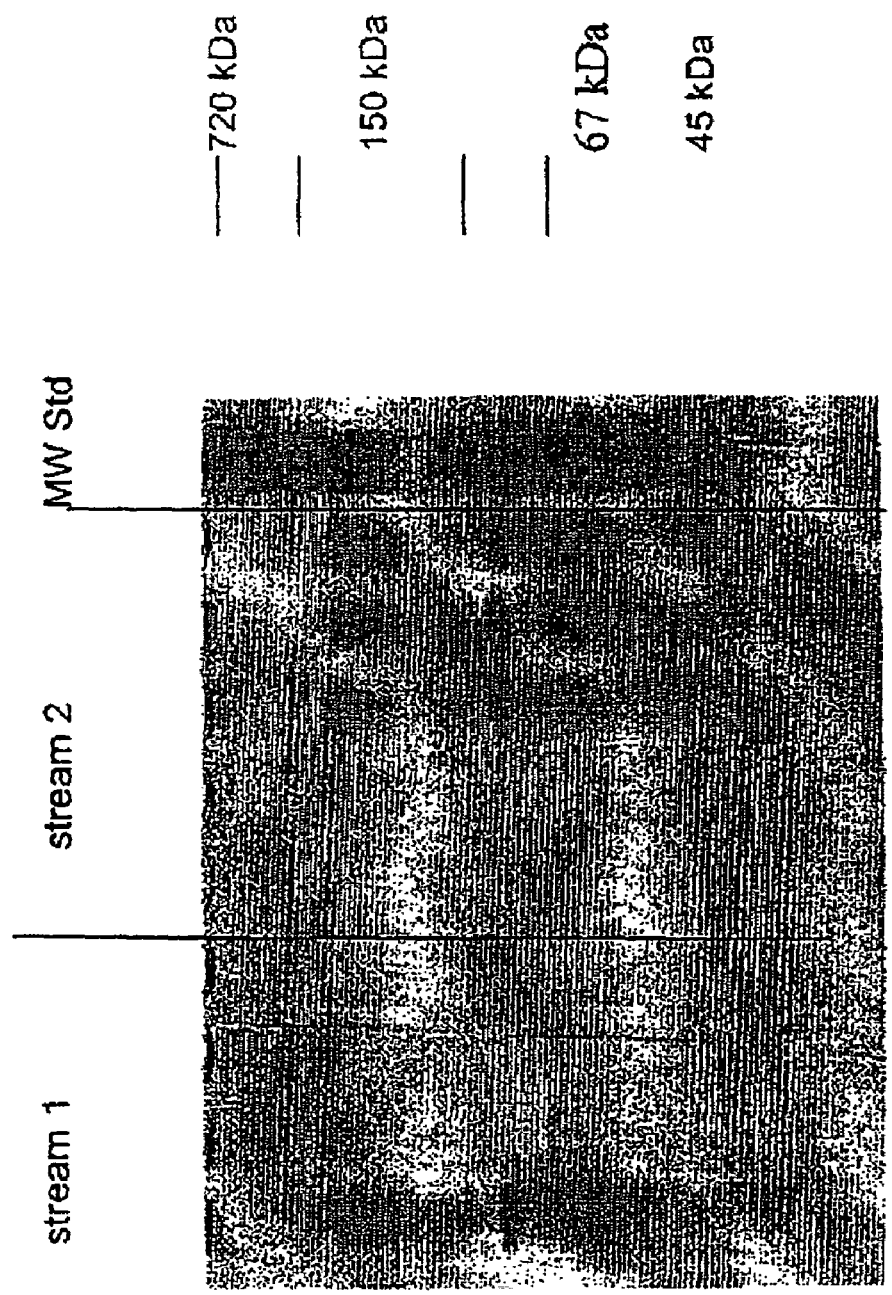
FIG. 6 is a polyacrylamide gel electrophoresis (PAGE) gel analysis of the protein separation described in Example 29.

Bovine serum albumin (BSA) and ovalbumin (Ovalb) were tested for protein transfer across the membranes from stream 1 to stream 2. FIG. 6 is a PAGE gel which shows complete protein transfer in less than 10 minutes across a 5% (w/v) PVAl membrane crosslinked with glutaraldehyde at 6.8% (w/w). Lanes 1–4 show protein fractions from stream 1 at 10 minute intervals. Lanes 6–9 show protein fractions taken from stream 2 at 10 minute intervals. Lane 10 contains a range of molecular weight markers used to confirm the size of the separated components. The observed transfer suggests that the effective pore size of the membrane exceeds the 67 kDa size of BSA.

EXAMPLE 30

Protein Separation Using 20% (w/v) PVAl Crosslinked Membranes with Glutaraldehyde at 9.2% (w/w) in 40 mM Tris-Glycine Buffer, pH 9.0.

Figure 7:
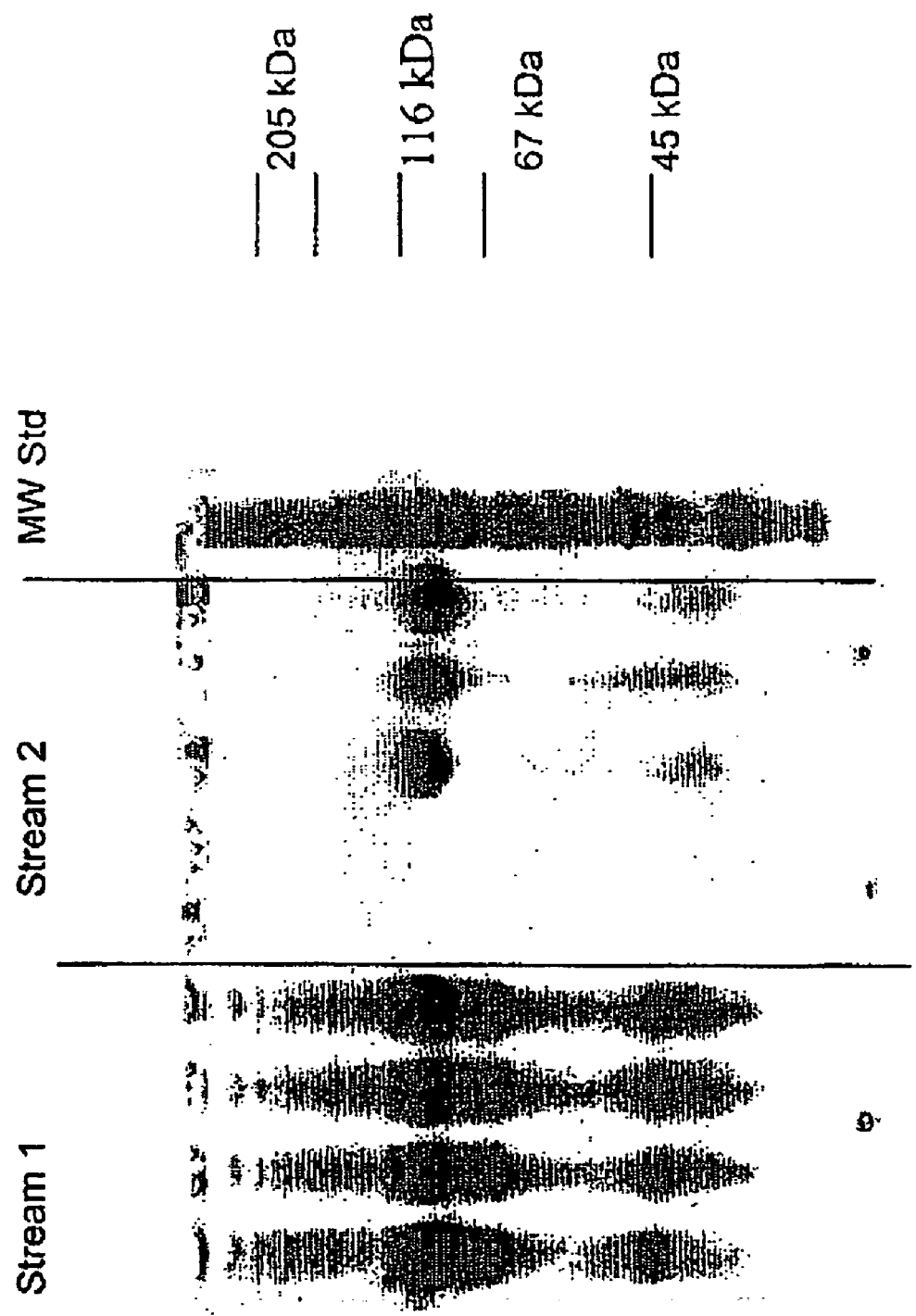
FIG. 7 is a PAGE gel analysis of the protein separation described in Example 30.

Cryo-precipitate was tested for protein transfer across the membranes from stream 1 to stream 2. FIG. 7 is a PAGE gel which shows successful transfer of some protein across a 20% (w/v) PVAl membrane crosslinked with glutaraldehyde at 9.2% (w/w). Lanes 1–4 show protein fractions from stream 1 at 10 minute intervals. Lanes 6–9 show protein fractions taken from stream 2 at 10 minute intervals. Human serum albumin (HSA) was successfully transferred along with smaller proteins. This was not complete for HSA and the reduced fibrinogen subunits (47 and 56 kDa are visible, the remaining subunits are masked by the strong HSA protein band) have remained in the stream 1 and were not present in the stream 2 samples. This indicates that the molecular weight cut off of the membrane is below 340 kDa (and above 67 kDa) in size. Lane 10 contains a wide range of commercially available molecular weight markers.

EXAMPLE 31

Protein Separation Using 20% (w/v) PVAl Crosslinked Membranes with Glutaraldehyde at 4.5% (w/w) in 40 mM Tris-Borate buffer, pH 8.5.

Figure 8:
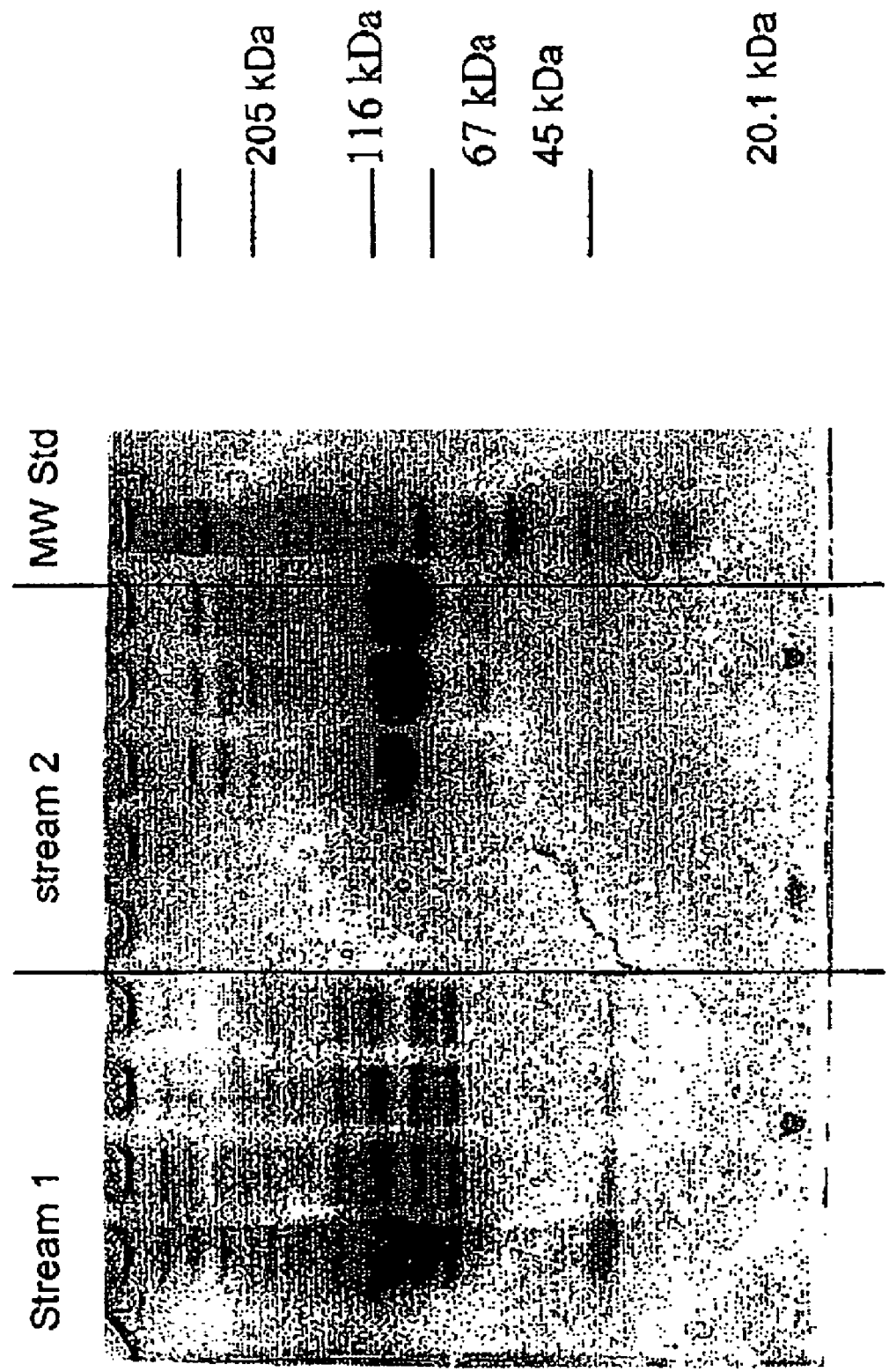
FIG. 8 is a PAGE gel analysis of the protein separation described in Example 31.

Cryo-precipitate was tested for protein transfer across the membranes from stream 1 to stream 2. FIG. 8 is a PAGE gel which shows successful protein transfer across a 20% (w/v) PVAl membrane crosslinked with glutaraldehyde at 4.5% (w/w). Lanes 1–4 show protein fractions from the stream 1 at 10 minute intervals. Lanes 6–9 show protein fractions taken from the stream 2 at 10 minute intervals. Lane 10 contains a wide range of commercially available molecular weight markers. Examination of the electrophoresis gel in lane 9 shows successful transfer of all other proteins than Fibrinogen from stream 1 reservoir to stream 2 reservoir. Fibrinogen bands remained in the stream 1 system, also evident using the Tris-Glycine buffer system. The prevention of the 340 kDa protein from passing through the membrane indicated size exclusion by the membrane.

EXAMPLE 32

Protein Separation Using 20% (w/v) PVAl Crosslinked Membranes with Glutaraldehyde at 9.2% (w/w) in 40 mM Tris-Borate Buffer, pH 8.5.

Figure 9:
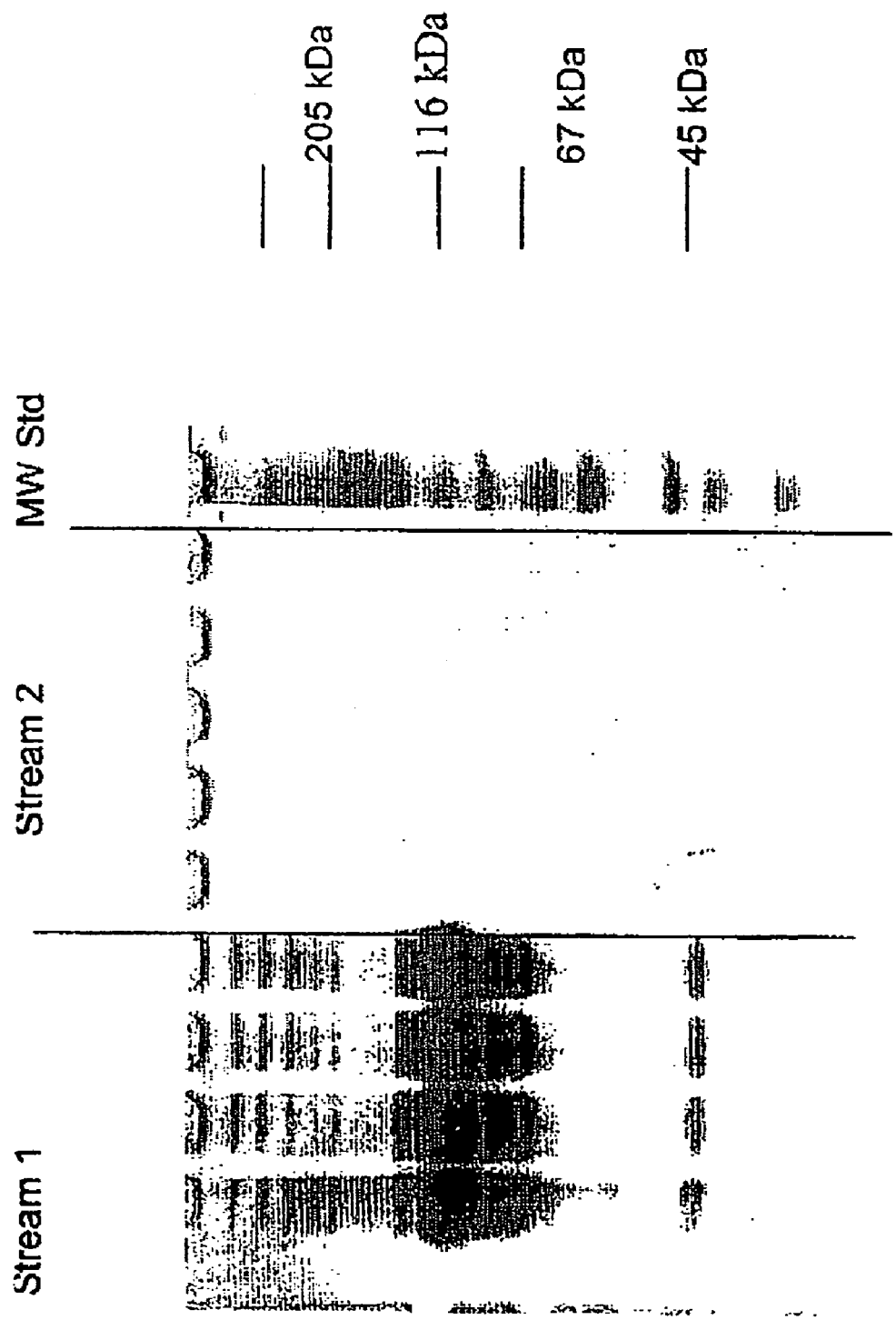
FIG. 9 is a PAGE gel analysis of the protein separation described in Example 32.

Cryo-precipitate was tested for protein transfer across the membranes from the stream 1 to the stream 2. FIG. 9 is a PAGE gel which shows no protein transfer at all across a 20% (w/v) PVAl membrane crosslinked with glutaraldehyde at 9.8% (w/w). Lanes 1–4 show protein fractions from stream 1 at 10 minute intervals. Lanes 6–9 show protein fractions taken from the stream 2 at 10 minute intervals. Lane 10 contains a wide range of commercially available molecular weight markers. The interaction between borate and PVAl combined with the increased concentration of PVAl and glutaraldehyde crosslinking tightens the effective pore size to such an extent that the proteins completely were restricted from transferring to stream 2. This induced size restriction that may facilitate concentration, desalting and buffer exchange processes for biomolecular samples.

EXAMPLE 33

Protein Separation Using 5% (w/v) PVAl Crosslinked Membranes with Glutaraldehyde at 4.5% (w/w) in 40 mM Tris-Glycine, pH 9.0 with the Substitution of Tris-Borate Buffer, pH 8.5.

Figure 10:
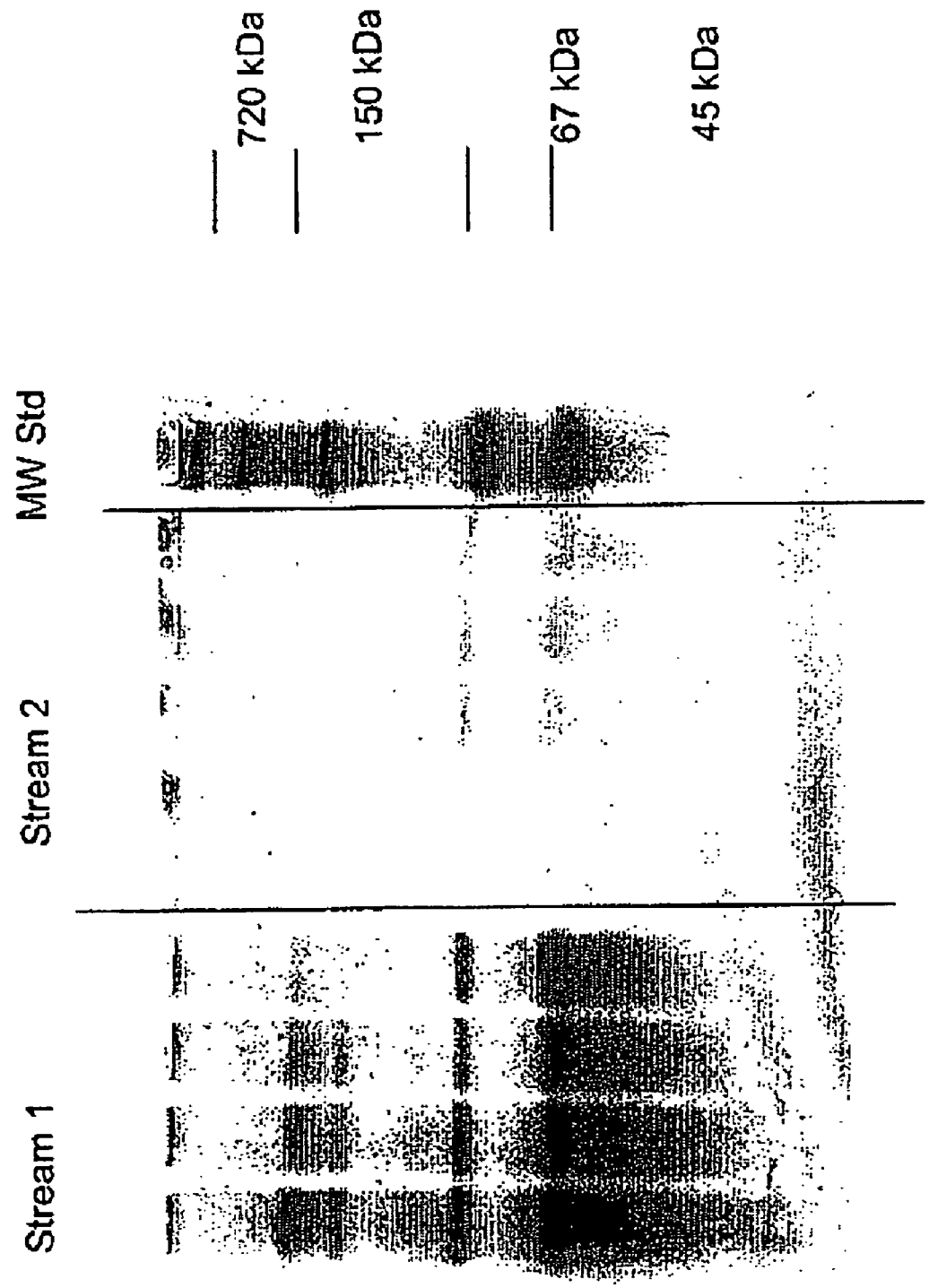
FIG. 10 is a PAGE gel analysis of the protein separation described in Example 33.

Protein samples containing Tris-Borate buffer were used substituted for Tris-Glycine buffer for this test. Tris-Glycine was used as the anodic buffer and the cooling buffer. BSA and Ovalb were tested for protein transfer across the membranes from stream 1 to stream 2. FIG. 10 is a PAGE gel which shows very slow protein transfer across a 5% (w/v) PVAl membrane crosslinked with glutaraldehyde at 4.5% (w/w). Lanes 1–4 show protein fractions from the stream 1 at 10 minute intervals. Lanes 6–9 show protein fractions taken from the stream 2 at 10 minute intervals. This gel demonstrates that borate used in the buffers significantly retards protein transfer through crosslinked PVAl membranes.

EXAMPLE 34

Protein Separation Using the alternative "3-membrane" Cartridge Containing 5% (w/v) PVAl Crosslinked Membranes with Glutaraldehyde at 4.5% (w/w) in 40 mM Tris-Glycine Buffer, pH 9.0.

Figure 11:
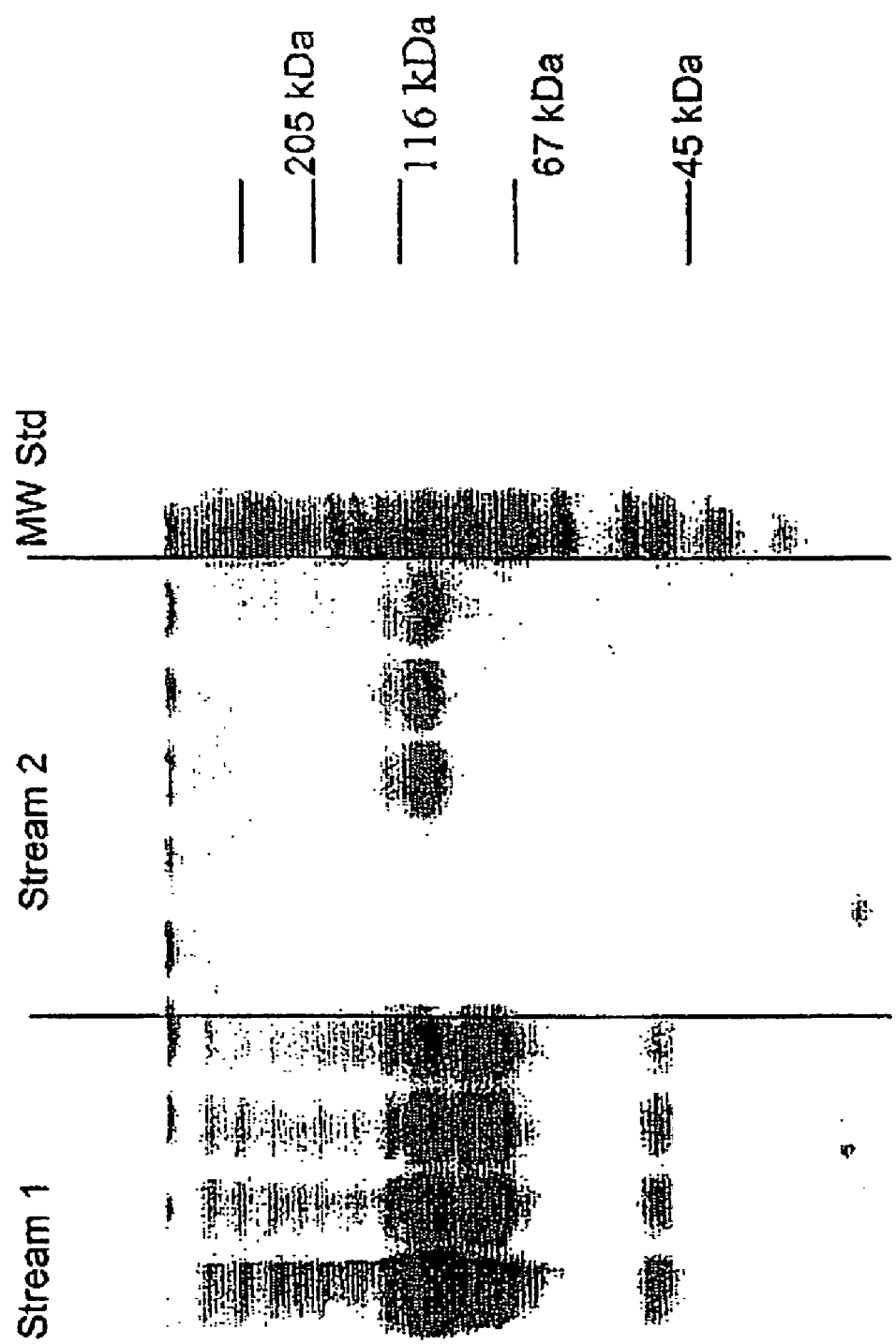
FIG. 11 is a PAGE gel analysis of the protein separation described in Example 34.

Cryo-precipitate was tested for protein transfer across the membranes from the stream 1 to the stream 2. FIG. 11 is a PAGE gel which shows successful transfer of some protein across a 5% (w/v) PVAl membrane crosslinked with glutaraldehyde at 4.5% (w/w). Lanes 1–4 show protein fractions from the stream 1 at 10 minute intervals. Lanes 6–9 show protein fractions taken from the stream 2 at 10 minute intervals. HSA was successfully transferred along with some smaller proteins. However, the larger proteins, including Fibrinogen were restricted from transfer from stream 1 to stream 2.

EXAMPLE 35

Protein Separation Using 5% (w/v) PVAl Crosslinked Membranes with Divinyl Sulfone at 54% (w/w) in 40 mM MES-BisTris, pH 6.85

Figure 12:
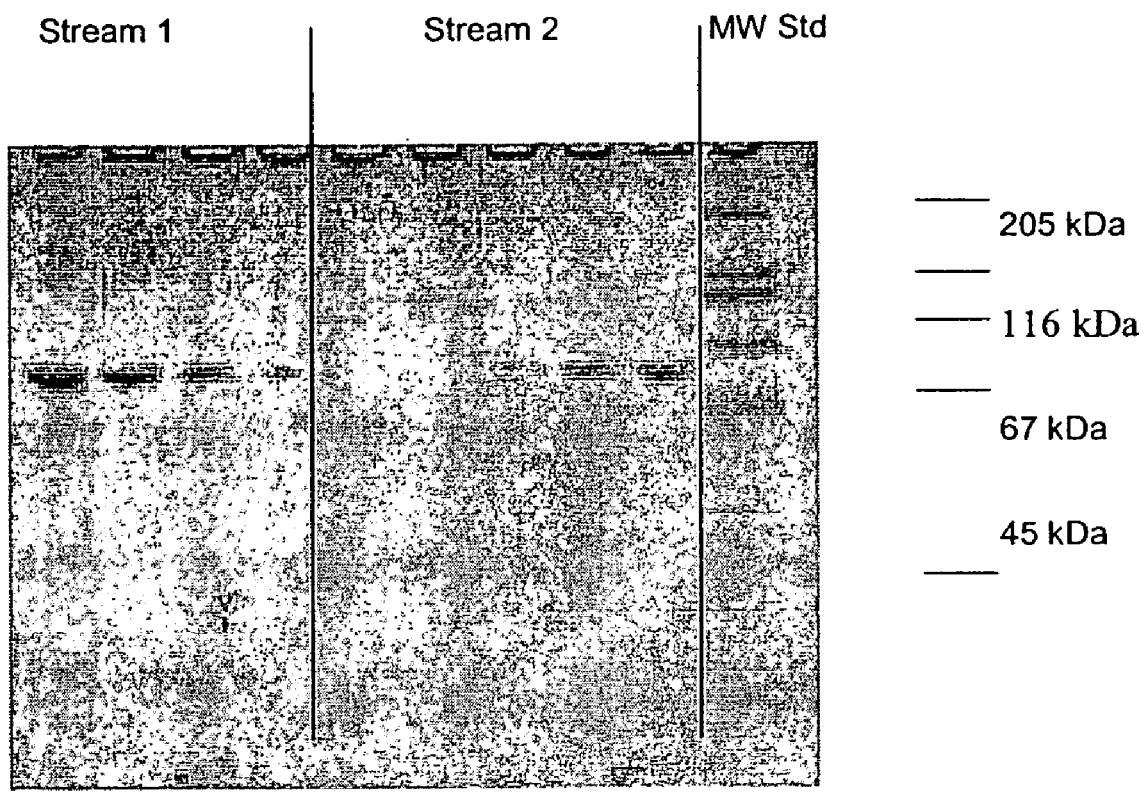
FIG. 12 is a PAGE gel analysis of the protein separation described in Example 35.

BSA was tested for protein transfer across the membranes from the stream 1 to the stream 2. FIG. 12 is a PAGE gel which shows protein transfer across a 5% (w/v) PVAl membrane crosslinked with divinyl sulfone at 45% (w/w). Lanes 1–4 show protein fractions from stream 1 at 10 minute intervals. Lanes 6–9 show protein fractions taken from the stream 2 at 10 minute intervals. This gel demonstrates that BSA protein transfer was successful through crosslinked PVAl membranes.

ANALYSIS OF MEMBRANES

EXAMPLE 36

Scanning Electron Microscopy (SEM)

Figure 13:
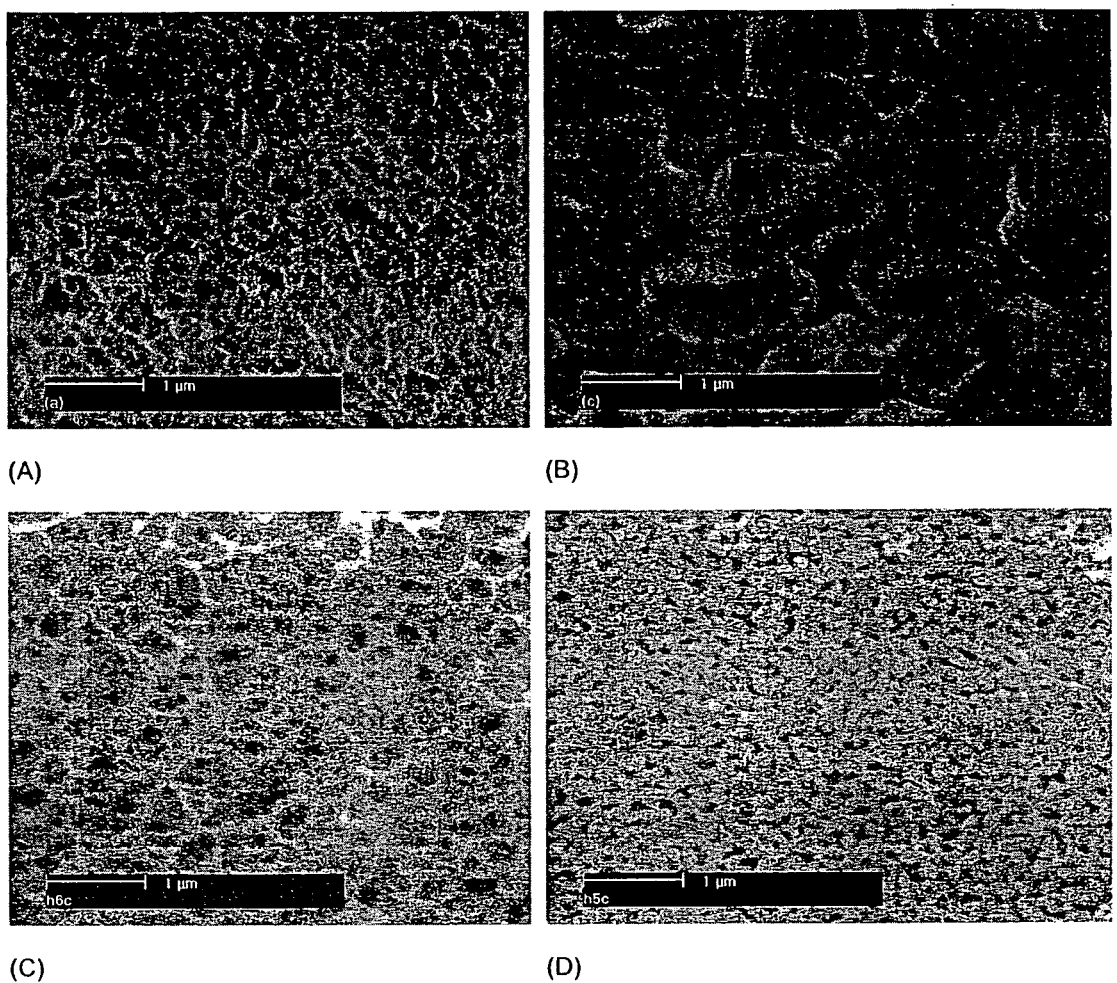
FIG. 13 is a scanning electron microgram (SEM) image of four embodiments of the present polymeric membrane described in Example 36. SEM 15000× magnification obtained for (A) 5% (w/v) PVAl crosslinked gel with glutaraldehyde at 4.5% (w/w); (B) 20% (w/v) PVAl crosslinked gel with glutaraldehyde at 9.2% (w/w); (C) 5% (w/v) PVAl crosslinked gel with divinyl sulfone at 18% (w/w); and (D) 5% (w/v) PVAl crosslinked gel with divinyl sulfone at 45% (w/w).

Gel structure morphology was examined using cryogenic SEM to prevent collapse of the gel network on drying. Gels 5×5 mm were mounted vertically on a SEM stub with a non-conductive glue and frozen at −198° C. in liquid nitrogen. The top was fractured off and the gel then warmed to −85° C. for 90 minutes whilst subliming water from the gel under reduced pressure. The sample was again cooled to −198° C. and images of the fractured gel taken at various magnifications. FIG. 13 shows pictures of PVAl gels crosslinked at different polymer concentrations. SEM images, 15000× magnification obtained for (A) 5% (w/v) PVAl crosslinked gel with glutaraldehyde at 4.5% (w/w), (B) 20% (w/v) PVAl crosslinked gel with glutaraldehyde at 9.2% (w/w) (C) 5% (w/v) PVAl crosslinked gel with divinyl sulfone at 18% (w/w) and (D) 5% (w/v) PVAl crosslinked gel with divinyl sulfone at 45% (w/w). All gel networks had uniform pore distributions and were clearly different to each other.

Methods

Purification of Glutaraldehyde Solution

Commercial glutaraldehyde solutions (25% w/v) were stirred with activated charcoal, filtered through basic alumina, filter aid and saturated with NaCl. This solution was extracted using diethyl ether and concentrated in vacuo. The crude glutaraldehyde was distilled under vacuum (45° C., 35 mm Hg) and diluted to make a 25% (w/v) solution with Milli Q water. This was stabilized with 100 ppm triethanolamine, purged with Ar(g) and stored at 4° C.

EXAMPLE 37

Protein Transfer Across 5% (w/v) PVA1 Crosslinked with Glutaraldehyde at 4.5% (w/w) Membranes Protein transfer for BSA was performed through 5% (w/v) PVA1, crosslinked with distilled glutaraldehyde at 4.5% (w/w) membranes. BSA (10 mL, 40 mg/100 mL) solution in 40 mM Tris-Glycine buffer was placed in the stream 1 reservoir, while the stream 2 was filled with 10 mL of 40 mM Tris-Glycine buffer. The pumps were turned on, and initial volumes noted. The voltage was set at 200 V and the current at 500 mA. Protein concentration was determined using UV-vis spectrophotometry at 280 nm.. Taking into account endoelectroosmosis effects, the amount of protein was calculated for the stream 1 and stream 2 reservoirs at time of sample removal. Protein yield was calculated based on the amount of protein in stream 2 with respect to the initial amount of protein. At time 60 min, BSA yield was determined to be approximately 78%, with below 10% residual in the stream 1.

EXAMPLE 38

Protein Transfer Across 5% (w/v) PVA1 Crosslinked with Divinyl Sulfone at 45% (w/w) Membranes Protein transfer for BSA was performed through 5% (w/v) PVA1, crosslinked with divinyl sulfone at 45% (w/w) membranes. BSA (10 mL, 40 mg/100 mL) solution in 40 mM MES-BisTris buffer was placed in the stream 1 reservoir, while the stream 2 was filled with 10 mL of 40 mM MES-BisTris buffer. The pumps were turned on, and initial volumes noted. The voltage was set at 200 V and the current at 500 mA. Protein concentration was determined using UV-vis spectrophotometry at 280 nm. Taking into account endoelectroosmosis effects, the amount of protein was calculated for the stream 1 and stream 2 reservoirs at time of sample removal. Protein yield was calculated based on the amount of protein in stream 2 with respect to the initial amount of protein. At time 60 min, BSA yield was determined to be approximately 65%, with below 20% residual in the stream 1.

Gradiflow™ is a trademark of Gradipore Limited, Australia.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application. It will be appreciated by those skilled in the art that numerous variations and/or modifications may be made to the present invention as shown in the specific embodiments without departing from the spirit and scope of the invention as broadly described. The present embodiments are, therefore, to be considered in all respects as illustrative and not restrictive.

What is claimed is:

1. A polymeric membrane prepared by a method comprising:
reacting a mixture comprising a pre-polymer having a plurality of crosslinkable moieties with a polyfunctional crosslinking agent, wherein the crosslinkable moieties are crosslinked with the polyfunctional crosslinking agent, wherein the weight range of the polyfunctional crosslinking agent in the mixture is between about 1% and about 1,500% w/w, and wherein the pre-polymer has a molecular weight range of about 20,000 to about 30,000.

2. The polymeric membrane according to claim 1, wherein the membrane is a hydrogel.

3. The polymeric membrane according to claim 1, wherein the pre-polymer is formed from a homopolymer or a copolymer.

4. The polymeric membrane according to claim 3, wherein the pre-polymer is substantially devoid of charge.

5. The polymeric membrane according to claim 4, wherein the pre-polymer is hydrophilic and water soluble.

6. The polymeric membrane according to claim 5, wherein the crosslinkable moieties of the pre-polymer are hydroxy groups.

7. The polymeric membrane according to claim 1, wherein the pre-polymer is a synthetic polymer formed by chain growth polymerization, condensation polymerization, or by both chain growth polymerization and condensation polymerization.

8. The polymeric membrane according to claim 7, wherein the synthetic pre-polymer is selected from the group consisting of poly(vinyl alcohol), partially esterified poly(vinyl alcohols), copolymers of poly(vinyl alcohols), polymers of hydroxyethylmethacrylate and hydroxyethylacrylate, and polymers of glycidylacrylate and glycidylmethacrylate.

9. The polymeric membrane according to claim 8, wherein the pre-polymer is poly(vinyl alcohol).

10. The polymeric membrane according to claim 1, wherein the pre-polymer is a natural polymer.

11. The polymeric membrane according to claim 10, wherein the natural pre-polymer is selected from the group consisting of starch, dextrans, cellulose derivatives, agarose, modified agaroses, and other polysaccharides.

12. The polymeric membrane according to claim 1, wherein the polyfunctional crosslinking agent contains at least 2 functional groups that are capable of reacting with the crosslinkable moieties of the pre-polymer to form covalent bonds.

13. The polymeric membrane according to claim 1, wherein the polyfunctional crosslinking agent is substantially uncharged and does not result in a significant degree of charged groups via side reactions.

14. The polymeric membrane according to claim 1, wherein the polyfunctional crosslinking agent is hydrophilic.

15. The polymeric membrane according to claim 1, wherein the polyfunctional crosslinking agent is selected from the group consisting of dialdehydes, di-isocyanates, diacids, water soluble epoxides, diesters, diacid halides, free or etherified N-methylol ureas or N-methylol melamines, dihalogen compounds, epichlorhydrin, dianhydrides, dicarboxylic acids, citric acid, olefinic dialdehydes, phthalaldehyde, 1,3-dichloroacetone, and 1,3-dichloroisopropanol.

16. The polymeric membrane according to claim 15, wherein the polyfunctional crosslinking agent is a dialdehyde.

17. The polymeric membrane according to claim 15, wherein the polyfunctional crosslinking agent is selected from the group consisting of glutaraldehyde, 2-hydroxyhexane-1,6-dial, malonic dialdehyde, succinic dialdehyde, and hexane-1,6-dial.

18. The polymeric membrane according to claim 17, wherein the polyfunctional crosslinking agent is glutaraldehyde.

19. The polymeric membrane according to claim 1, wherein the pre-polymer is a poly(vinyl alcohol) and the polyfunctional crosslinking agent is glutaraldehyde.

20. The polymeric membrane according to claim 1, wherein the weight range of the polyfunctional crosslinking agent in the polymeric membrane is between about 1% and about 20% w/w.

21. The polymeric membrane according to claim 1, wherein the polyfunctional crosslinking agent is a dialdehyde and wherein the weight range of the dialdehyde in the polymeric membrane is between about 1% and about 20% w/w.

22. The polymeric membrane according to claim 21, wherein the weight range of the dialdehyde is between about 4% and about 15% w/w.

23. The polymeric membrane according to claim 22, wherein the weight range of the dialdehyde is between about 4.5% and about 9.2% w/w.

24. The polymeric membrane according to claim 1, wherein the polyfunctional crosslinking agent is a divinyl sulfone and wherein the weight range of the divinyl sulfone in the mixture is between about 20% and about 60% w/w.

25. The polymeric membrane according to claim 24, wherein the weight range of the divinyl sulfone is between about 40% and about 50% w/w.

26. The polymeric membrane according to claim 25, wherein the weight range of the divinyl sulfone is about 45% w/w.

27. The polymeric membrane according to claim 25, wherein the weight range of the divinyl sulfone is between about 45% and about 50% w/w.

28. The polymeric membrane according to claim 1, wherein the polyfunctional crosslinking agent is a glycol diglycidyl ether and wherein the weight range of the glycol diglycidyl ether in the mixture is between about 500% and about 1,500% w/w.

29. The polymeric membrane according to claim 1, wherein the percentage of the reacted pre-polymer in the membrane is about 5% to about 40% w/w.

30. The polymeric membrane according to claim 29, wherein the percentage of the reacted pre-polymer in the membrane is about 10% to about 20% w/w.

31. The polymeric membrane according to claim 1, wherein the membrane is supported by a substrate.

32. The polymeric membrane according to claim 31, wherein the substrate is a woven material, a non-woven material, or a textile.

33. The polymeric membrane according to claim 31, wherein the substrate is in the form of a sheet or web.

34. The polymeric membrane according to claim 31, wherein the polymeric membrane is a layer formed on the surface of the substrate, or the substrate is incorporated within the polymeric membrane.

35. The polymeric membrane according to claim 31, wherein the substrate is formed from a material selected from the group consisting of poly(vinyl alcohol), polyethyleneteraphthalate, nylon and fibreglass, cellulose, and cellulose derivatives.

36. The polymeric membrane according to claim 35, wherein the substrate is heat bonded polyethyleneteraphthalate, optionally pre-treated with a non-ionic surfactant.

37. The polymeric membrane according to claim 31, wherein the substrate has hydrophilic characteristics.

38. The polymeric membrane according to claim 37, wherein the substrate is poly(vinyl alcohol) paper.

39. The polymeric membrane according to claim 1, wherein the crosslinkable moieties are treated with a coordinating agent.

40. The polymeric membrane according to claim 39, wherein the coordinating agent is in the form of a buffer.

41. The polymeric membrane according to claim 39, wherein the coordinating agent is borate.

42. A method for forming a polymeric membrane, comprising the steps of:
reacting a mixture comprising a pre-polymer having a plurality of crosslinkable moieties;
with a polyfunctional crosslinking agent;
wherein the crosslinkable moieties are crosslinked with the polyfunctional crosslinking agent, wherein the weight range of the polyfunctional crosslinking agent in the mixture is between about 1% and about 1.500% w/w, and wherein the pre-polymer has a molecular weight range of about 20,000 to about 30,000.

43. A method for separating molecules comprising the steps of:
providing a polymeric membrane according to claim 1; and
subjecting the polymeric membrane and a sample comprising a mixture of molecules to be separated to a separation technique whereby the molecules are separated.

44. The method according to claim 43, wherein the molecules to be separated are a charged species, or a species capable of bearing a charge.

45. The method according to claim 44, wherein the molecules to be separated are bio-molecules.

46. The method according to claim 45, wherein the bio-molecules are selected from the group consisting of proteins, peptides, DNA and RNA.

47. The method according to claim 43, wherein the separation technique is an electrophoretic technique.

48. The method according to claim 47, wherein the electrophoretic technique separates molecules on the basis of size, charge, or both size and charge.

49. The method according to claim 43, wherein the sample comprises a protein and a borate in solution, and the protein is concentrated.

50. A cartridge suitable for use in an electrophoretic device, comprising the polymeric membrane according to claim 1.

51. An electrophoretic device comprising at least one polymeric membrane according to claim 1 disposed between two membranes.

* * * * *